United States Patent
Peeters

(10) Patent No.: US 6,778,858 B1
(45) Date of Patent: Aug. 17, 2004

(54) COCHLEAR IMPLANT

(75) Inventor: Stefaan Peeters, 'S Gravenwezel (BE)

(73) Assignee: Advanced Bionics N.V. (BE)

(*) Notice: Subject to any disclaimer, the term of this patent is extended or adjusted under 35 U.S.C. 154(b) by 48 days.

(21) Appl. No.: 10/088,194
(22) PCT Filed: Sep. 18, 2000
(86) PCT No.: PCT/BE00/00109
§ 371 (c)(1),
(2), (4) Date: Apr. 18, 2002
(87) PCT Pub. No.: WO01/19304
PCT Pub. Date: Mar. 22, 2001

(30) Foreign Application Priority Data

Sep. 16, 1999 (BE) .............................. 9900621

(51) Int. Cl.$^7$ .............................................. A61F 11/04
(52) U.S. Cl. ............................................... 607/57
(58) Field of Search ........................... 607/55, 56, 57, 607/137; 600/25

(56) References Cited

U.S. PATENT DOCUMENTS 5,899,931 A    5/1999  Deschamp et al.

FOREIGN PATENT DOCUMENTS

| EP | 0 241 101 | 10/1987 |
| WO | WO 97/09012 | 3/1997 |
| WO | WO 97/38653 | 10/1997 |
| WO | WO 98/49775 | 11/1998 |

OTHER PUBLICATIONS

David H. Liang et al., IEEE Transactions on Biomedical Engineering, "A Method of Evaluating the Selectivity of Electrodes Implanted for Nerve Stimulation", vol. 38, No. 5, May 1991, pp 443–449.

Primary Examiner—Scott M. Getzow
(74) Attorney, Agent, or Firm—Piper Rudnick LLP

(57) ABSTRACT

A cochlear implant comprising a storage buffer in which sampling values derived from a sound signal are saved. The storage buffer is connected to a multichannel waveform generator, in which data for a stimulation strategy are saved. Reading and writing to the peak hold buffer occurs asynchronously.

21 Claims, 14 Drawing Sheets

Example of centerfrequency distribution as a function of place. This for 31 channels

| Number | mm distance from RW | Hz centerfrequency | Hz bandwidth |
|---|---|---|---|
| 1 | 33 | 100 | 36 |
| 2 | | 136 | 40 |
| 3 | | 176 | 44 |
| 4 | | 220 | 49 |
| 5 | | 270 | 55 |
| 6 | | 324 | 61 |
| 7 | | 385 | 67 |
| 8 | | 452 | 75 |
| 9 | 26 | 527 | 83 |
| 10 | | 610 | 92 |
| 11 | | 702 | 102 |
| 12 | | 804 | 113 |
| 13 | | 918 | 126 |
| 14 | | 1044 | 140 |
| 15 | 20 | 1183 | 155 |
| 16 | | 1339 | 172 |
| 17 | | 1511 | 191 |
| 18 | | 1702 | 212 |
| 19 | | 1914 | 236 |
| 20 | | 2150 | 261 |
| 21 | 15 | 2411 | 290 |
| 22 | | 2702 | 322 |
| 23 | | 3024 | 358 |
| 24 | | 3381 | 397 |
| 25 | | 3778 | 441 |
| 26 | 10 | 4219 | 489 |
| 27 | | 4708 | 543 |
| 28 | | 5251 | 603 |
| 28 | | 5853 | 669 |
| 29 | | 6522 | 742 |
| 30 | | 7265 | 824 |
| 31 | 5 | 8089 | 915 |

*Fig. 5*

Sampling waveform a  Biphasic pulse b  Asymmetric biphasic pulse c  Biphasic pulse with Time Gab d  Asym with Time Gab e  Composed pulse f  Triphasic pulse g  Composed amplitude pulse h  Monophasic pulse duty cycle 100 % i  Monophasic pulse duty cycle n %

$$I_{offset}^{n} = \frac{C_m^n I_p^n - C_p^n I_m^n}{C_m^n - C_p^n}$$

Interaction and correction

Interaction and correction

COCHLEAR IMPLANT

RELATED APPLICATION

This is a §371 of International Application No. PCT/BE00/00109, with an international filing date of Sep. 18, 2000, which is based on Belgian Patent Application No. 9900621, filed Sep. 16, 1999.

FIELD OF THE INVENTION

The invention relates to a cochlear implant, comprising a signal processor, having a set of audio channel units and being provided for the conversion of sound signals, according to a frequency related tonotopic division, each audio channel being provided for applying a frequency related filtering to said sound signal, each audio channel having an output associated with a first sampling unit, provided for sampling at an audio channel associated sampling rate, the signal output by its associated audio channel unit and writing sampled signal values into a storage buffer, each sampling unit being connected with said storage buffer, provided for temporarily storing said sampled signal values, said storage buffer being connected with a waveform generator comprising at least one stimulation channel, said waveform generator and said storage buffer being connected to a read signal generator, is provided for generating read signals enabling to read the stored sampled signal values from said storage buffer, said waveform generator being provided for retrieving under control of said read signal, said sampled signal values of each audio channel from said storage buffer and for generating based on said sampled signal values waveforms having a time period and a wave pattern, said waveform generator being provided for stimulating by means of said waveforms electrode contacts of said cochlear implant.

BACKGROUND

A cochlear implant is well known and is used to restore auditory perception, at least partially, to the deaf and hard-of-hearing. Cochlear implants make it possible to create auditory sensation, by generating electric field gradients in the area of the peripheral nerve fibres of the auditory nerve bundle. This bundle contains approximately 30,000 individual afferent nerve fibres, normally linked to approximately 4,500 internal hair cells. The sound signals are picked up by a microphone, converted into digital signals, and processed by the signal processor in order to activate different stimulation channels, which stimulate different groups of nerve fibres of the auditory nerve. The area where the initialisation of action potentials takes place is referred to as the excitation area. The initialisation site of the action potential can be located either in the dendrites, at the site of the cell body, at the level of the axons or any combination. To ensure that each stimulation channel doesn't lack essential information, due to the different timings in writing by the signal processor and reading by the waveform generator, the buffer is implemented as a temporal peak hold storage.

A drawback of the known cochlear implants is that there is no clear distinction between sound processing part and stimulation channels. As a result, the stimulation strategy i.e. the manner according to which the various stimulation channels are activated, cannot be chosen independently of the signal processing.

It would therefore be advantageous to provide a cochlear implant, which enables a strategy which takes into account the patient dependent data, the case history (like temporal field interaction) and the electric field interaction during simultaneous stimulation of different stimulation channels.

SUMMARY OF THE INVENTION

For this purpose a cochlear implant is characterised in that said signal processor comprises a stimulation channel configuration unit connected with said storage buffer and provided for configurating stimulation channels in order to create electrical fields along auditory neural structures, said stimulation channel configuration unit being connected to said electrode contacts and further provided to allocate to each stimulation channel at least two of said electrode contacts, to each stimulation channel there being assigned a memory element provided for storing a waveform platform and a wave duration according to and during which an intensity value determined on the basis of the sampled signal value attributed to the considered stimulation channel is applicable to the electrode contacts allocated to the considered stimulation channel, said memory element being further provided for storing a maximum value for said intensity value indicating a maximum field strength for the considered stimulation channel and a first and second field identifier identifying a field spread in a basal and apical direction relative to a position of the stimulation channel.

In order to carry through the best possible conversion of the stored sampled signal values, into current or voltage stimulation waveforms for the N different stimulation channels, it is necessary to determine a suitable stimulation strategy. This strategy should take into account the patient-dependent data, the case history (like temporal field interaction) and the electric field interaction during simultaneous stimulation of different stimulation channels. In order to take this into account a cochlear implant according to the invention comprises M (M>1) electrode contacts and a signal processor having a set of N audio channel units and being provided for the conversion, according to a frequency related tonotopic division, of sound signals, each audio channel being provided for applying a frequency related filtering to said sound signal, each audio channel having an output associated with a second sampling unit provided for sampling at an audio channel associated sampling rate the signal output by its associated audio channel unit and writing them into a storage buffer, each second sampling unit being connected with said storage buffer provided for temporarily storing sampled signal values supplied by its associated second sampling unit.

Such a cochlear implant is characterised in that said storage buffer is connected with a stimulation channel configuration unit, provided for defining stimulation channels in order to create electrical fields along auditory neural structures, said stimulation channel configuration unit being further provided to allocate to each stimulation channel at least two of said electrode contacts, to each stimulation channel a memory element is assigned, provided for storing a waveform pattern and a wave duration according to and during which an intensity value determined on the basis of the sampled signal value attributed to the considered stimulation channel is applicable to the electrodes assigned to the considered stimulation channel, said memory element being further provided for storing a maximum value for said intensity value indicating a maximum field strength for the considered stimulation channel and a first and second field identifier, identifying a field spread in a basal and apical direction relative to a position of the electrode contacts of the considered stimulation channel.

The stimulation channel configuration unit makes it possible to establish specific stimulation channel configurations and specific stimulation intensity values and waveforms for each patient and store them.

A second preferred embodiment of a cochlear implant according to the invention is characterised in that it comprises a stimulation sequence identifier, provided for identifying a set of groups of stimulation channels which are simultaneously stimulatable, the stimulation channels of a same group being selected in order to enable a neural stimulation at neural excitation locations which match with neural excitation locations that would be obtained if the individual stimulation channels of the group would have been stimulated sequentially in time, said stimulation sequence identifier being further provided for cyclically stimulating said groups of stimulating channels. Simultaneous stimulation of several auditory neural structures thus becomes available. In such a manner, a more efficient stimulation strategy can be obtained leading to a better audible result for the patient.

A third preferred embodiment of a cochlear implant according to the invention is characterised in that it comprises an ordering unit provided to order the groups within the set according to a sequence defining the order according to which the different groups are sequentially stimulated. By arranging the groups, a more efficient use of the stimulation channels is obtained.

Preferably, a time frame is assigned to each group of said set in such a manner, that the time frame of the assigned group is at least equal to the waveform duration of the stimulation channel within the considered group having the largest waveform duration. An efficient time sharing is thus obtained.

BRIEF DESCRIPTION OF THE DRAWINGS

The invention will now be described in more detail with reference to the drawings showing preferred embodiments of a cochlear implant according to the invention. In the drawings:

FIG. 5 shows an example of the frequency distribution for N=31 audio channels;

Figure 1:
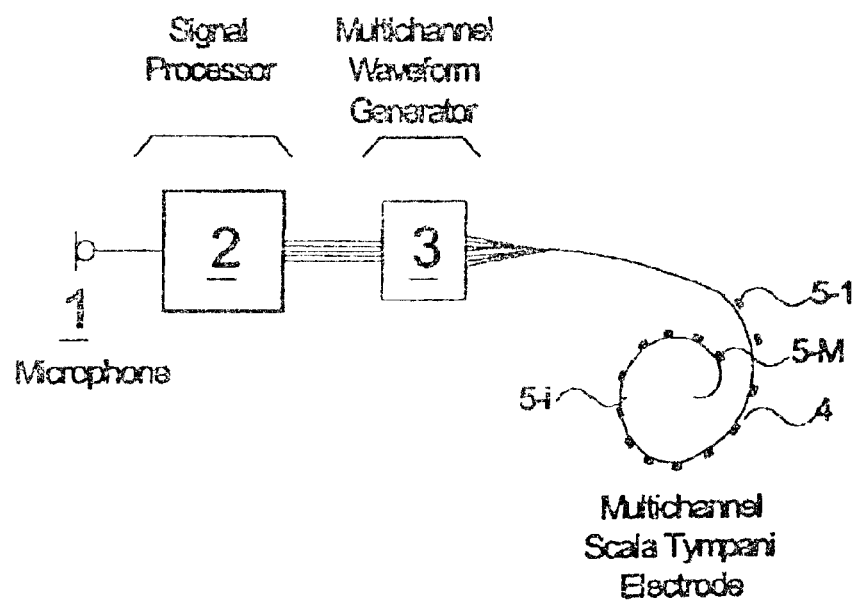
FIG. 1 shows a schematic representation of a cochlear implant.

The cochlear implant, represented in FIG. 1, comprises a signal processor 2, having an input connected to a microphone's or auxiliary input 1 for receiving a second signal. The signal processor converts, by means of an A/D converter, the analog sound signal picked up by microphone, first into a digital signal, which is then converted into a sequence of N electrical signals, according to a frequency related tonotopic division. The signal processor is connected to a waveform generator 3 which is also connected to a series of M (M>1) electrode contacts 5 housed in a carrier 4 made of a flexible biocompatible material such as silicone. This carrier or electrode array is implanted in the vicinity of the auditory nerve. Some contacts (for example, surfaces at the implant-package, etc.) are placed further away from the nerve fibres.

The electrical currents, applied on the electrode surfaces, create electrical field gradients along nerve fibres of the auditory nerve or neural structures. Based on the spatial organisation of the individual auditory nerve fibres in the cochlea, electrical fields of different stimulation channels result in activating various groups of nerve fibres. The activated nerve fibres fire action potentials and transmit these to higher auditory centers. The higher auditory centers process the parallel information, which the consciousness center then experiences as auditory information with different pitch sensations, loudness sensation, etc.

The nerve action potential is an "all or nothing" signal and as such consequently does not contain information. The underlying generated time patterns and the places of initialisation determine perception.

Figure 2:
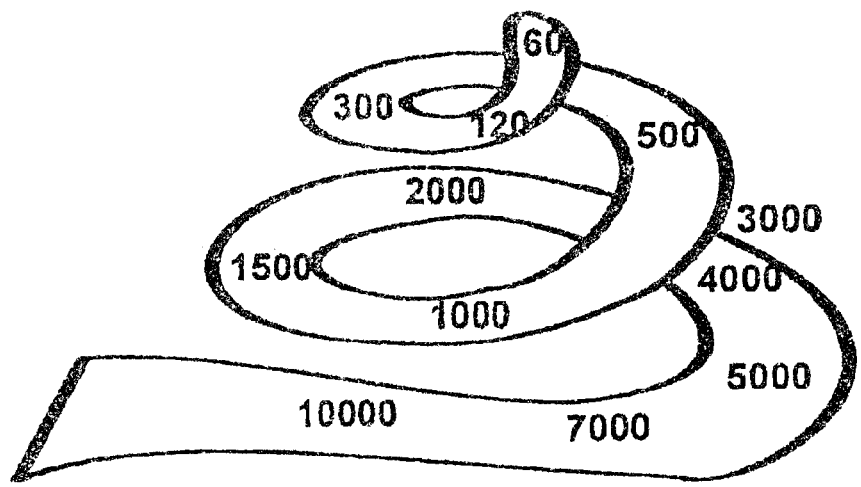
FIG. 2 shows the frequency dependent tonotopic organisation of the cochlea with the position of the frequency-specific zones.

The normal internal cochlear structures, such as the Basilar membrane (BM) with the organ of Corti, play a crucial role in the conversion of the sound evoked mechanical movement to action potentials. The Basilar membrane performs a (non linear) filtering, as a result of which low-frequency information mainly stimulates the nerve fibres situated in the apical region (at the end) of the cochlea, while high-frequency signals activate the basally located nerve fibres. In this manner, the auditory nerve fibres carry frequency dependent information due to the tonotopic organisation as illustrated in FIG. 2. In case of malfunctioning of the mechanical to electrical conversion of the cochlea, this frequency-based tonotopy can be imitated by electrically activating electrode surfaces at various places along the nerve fibres. The non-linear (NL) behaviour of the BM results in a compression, with a compression factor of 2 to 3 around the region of maximum vibration.

Figure 3:
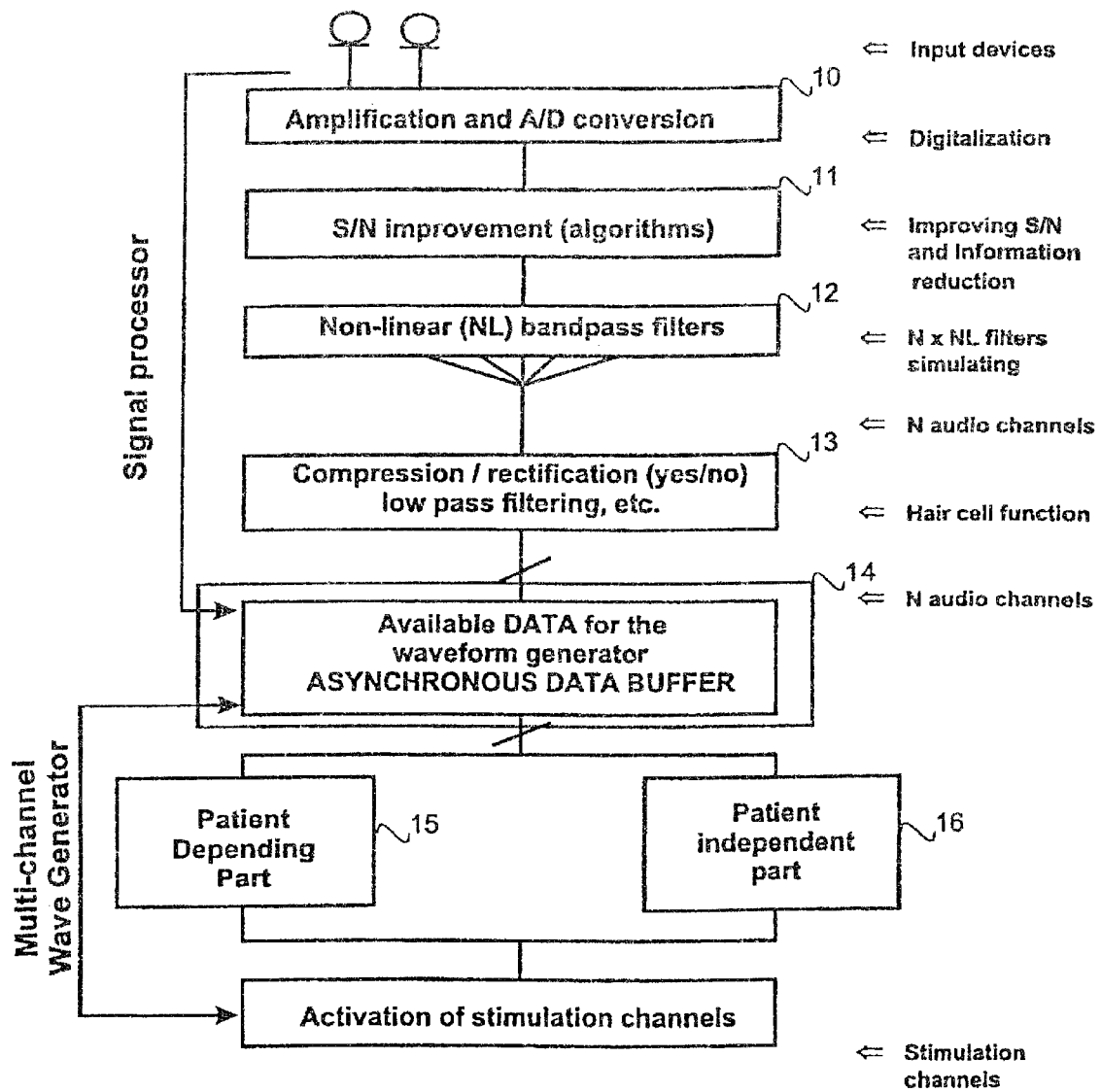
FIG. 3 shows a schematic representation of the processing of the sound signal processor, as well as a multichannel waveform generator.

FIG. 3 gives, by means of a flow chart, a schematic example of how the signal processor 2 processes the signals picked up by the input devices. It also gives a schematic representation of the multichannel waveform generator 3 with its R (R≧1) stimulation channels and, which determines the stimulation strategy. After analog to digital conversion (10), the signal to noise ratio (S/N) of the signal is improved and information reduced by, for example, taking in account the normal masking curves of the auditory system (11).

The electrical analog of the acoustic signal is split up into N audio channels. Non linear filters, which take into account the tonotopic position of the nerve fibres, separate (12) the signal into a sequence of electrical signals. The audio channels process further the output signals of the various frequency bands (13), by applying i. a. a compression, possible rectification, filtering, etc., in order to obtain a signal value per audio channel. Each audio channel has an output associated with a first sampling unit provided for sampling at an audio channel associated sampling rate the signal output by that channel. Sampled values of the output signals of the audio channels are directly linked to the stimulation levels in one or more corresponding stimulation channels. The sampled signal values produced by the specific output signal per audio channel are temporarily saved in a data storage buffer (14). The way in which this information supplied by audio channels is processed by the waveform generator and passed to its stimulation channels, in order to stimulate various groups of nerve fibres is referred to as stimulation strategy.

The waveform generator contains both patient-dependent (15) and patient-independent (16) data for processing and controlling the activation of the various stimulation channels.

Figure 4:
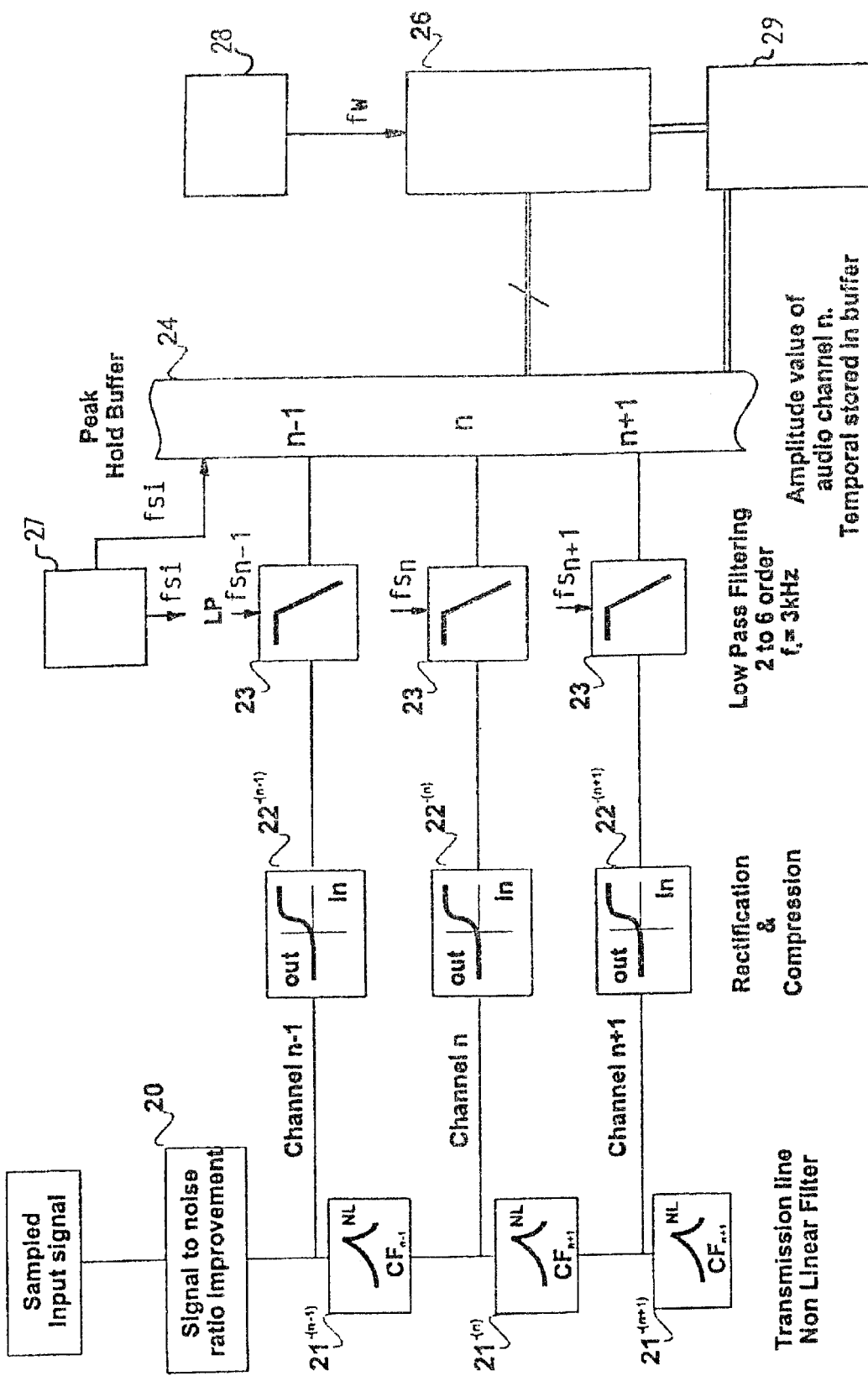
FIG. 4 shows an example of a signal processing of the sound signal.

FIG. 4 shows an example of how the sound signal i split up by the signal processor into N (N≧1) audio channels and processed. After reduction of the signal, based on auditory masking (20), the sound signal is split by an N non-linear (transmission line) filters 21 into N audio channels. The characteristics of the non-linear filters reflect the properties of the basilar membrane and the active feedback mechanisms, like compression around the characteristic place. FIG. 5 shows an example of how the frequency distribution for N=31 audio channels could be. Each audio channel is provided with a rectifier/compression unit 22, which is connected to a high order low-pass filter 23, e.g. $2^{th}$ to $6^{th}$ order. The compression unit simulates the function performed by the inner-, outer hair cells, etc., while the low-pass filters in each channel simulate the internal hair cell filtering and other physiological effects. Each filter 23 is connected to the data storage buffer 24, in which the sampled signal values, produced by the audio channels, are stored. The outputs of the audio channels 23 are presented to the data buffer at audio-channel dependent sampling frequencies (fsi) controlled by the first sampling unit 27 associated with the signal processor unit. The new presented values are stored in the hold buffer under condition that the absolute value of the stored value is lower than the absolute value of the new sampled available data of the corresponding audio channel. For this purpose a preset value, for example, a zero or minimum value, is stored in the storage buffer under control of a read signal generated by the waveform, each time after that a sampled signal value is read from the storage buffer 24. When a new value is supplied by one of the audio channel filters 23 to the storage buffer, that new value is compared by means of a comparator, which is part of the signal processor, to the sampled signal value stored in the storage buffer for the considered audio channel. When the supplied new value has a higher absolute signal value than the stored signal value, the comparator generates a writing signal. The new signal is then stored in the storage buffer under control of the writing signal. If the new value is lower than the stored one, no writing signal is generated and the new value is ignored. The storage buffer 24 is linked (by means of a channel-mapping function) to a stimulation channel of the waveform generator 26, which includes stimulation channels to which electrode contacts are attributed by the stimulation-channel-configuration unit. The channel-mapping function connects each audio channel to one or more stimulation channels.

Consequently, the analog input signal undergoes various processes, performed by the signal processor, in order to generate signal values for each of the stimulation channels to be activated. Since this involves fluctuating signals, these audio channel outputs show a waveform with amplitude maxima and minima. In order to prevent loosing important amplitude information related to the output signal of an audio channel between the time periods of successive stimulation of associated stimulation channels, the storage buffer has been implemented as follows. Before the signal processor writes the sampled data of an audio channel in the storage buffer, the comparator, connected to the signal generator and the data buffer, performs a comparison between the absolute value of the available sample and the stored absolute value corresponding this audio channel.

The absolute value saved in the data buffer for the $i^{th}$ audio channel in question (1≦i≦N) will be compared with the sampled absolute signal value delivered by the audio channel –i. If the $i^{th}$ absolute value saved in the data buffer is higher than or equal to the sampled absolute value delivered by the $i^{th}$ audio channel, then the latter value is not written to the data buffer, and the saved value is maintained. If, on the other hand, the value delivered by the audio channel is higher than the saved $i^{th}$ absolute value, then the sampled value of the $i^{th}$ audio channel is written to the buffer. This comparison is performed for each of the N channels when the first sampling unit of the signal generator gives a new sampled value at one of the audio channels outputs. The waveform generator reads the stored values on request from stimulation channels. When reading a stored value from the storage buffer the corresponding stored value is set to a preset value, which could be zero. In this manner, the storage buffer maintains the maximal available sampled data of an audio channel output between successive requests of a stimulation channel. When request signal rate is faster than or equal to the sampling rate the read data follows the sampled data. When request rate is lower than the sampling rate the read data corresponds with the maximum sampled data presented to the storage buffer between successive readings.

The signal values saved in the storage buffer are read by the waveform generator unit 26 under control of its own sampling unit 28 generating sampling signals fw and which functions totally independent and asynchronously from the sampling unit of the signal processor. By using the storage buffer, which temporarily stores values, the reading and writing of the signal values can be performed totally independently and asynchronously between audio channels and stimulation channels, so that the processing of the audio signal is no longer time linked to the stimulation strategy. The asynchronous reading and writing, and the storage buffer, make it possible to unlink the speech processing from the waveform generator and his stimulation strategy and allows to combine in an easy way different signal processing systems with different stimulation strategies.

The waveform generator controls the translation of the values stored in the storage buffer 24 to stimulation patterns at the level of the multi-surface-contact electrode. For this purpose, the waveform generator unit 26 constructs a series of R stimulation channels, taking into account patient-dependent data, the patient's case history, stimulation history, and the temporal and simultaneous electric field interaction during stimulation, etc..

Figure 6:
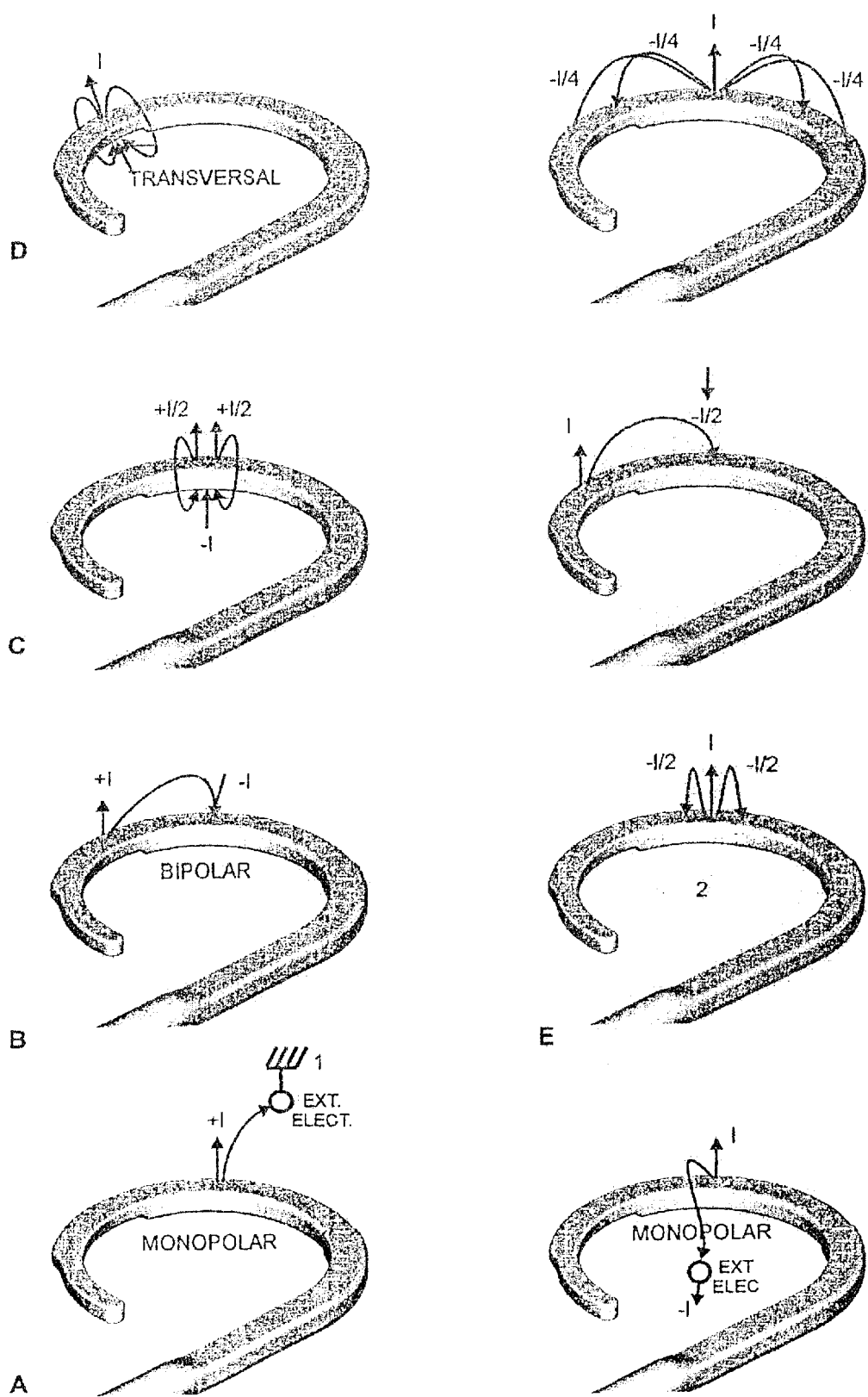
FIG. 6 shows examples of electrode contact configurations defined by the stimulation configuration unit.

Electrical stimulation requires a minimum of two of the M electrode contacts to form a complete current path. FIG. 6 illustrates a number of configurations where surface contacts are combined and associated with a stimulation channel.

For example in case of a monopolar (6a) configuration, one of the electrode contacts is usually placed in a position at a relatively long distance (relative to the distance between one of the contacts in the electrode array and the nerve fibres) from the second electrode contact.

For a bipolar (6b) configuration, the electrode contacts are placed closer together along the multi surface electrode array. Other configurations are possible, such as radial (6c) and transversal (6d) stimulation configurations, etc. More than 2 contacts can be involved, as an example using three or more contacts a quadrupole configuration can be obtained (6e).

A stimulation channel can use any combination of electrode contacts, which stimulated together, creates an electric excitation field along the auditory nerve fibres by means of injected currents (electric charges). Electrode contacts associated to a channel are connected with a voltage or current source or grounded to a reference. The individual values of the voltages and currents associated with the contacts of a stimulation channel can be any fraction and polarity relative to the controlling value of this stimulation channel when stimulating. For example, FIG. 6c shows a contact configuration where two side-by-side contacts are connected with current sources with a value of each +½ of the controlling value I, while the longitudinal electrode is connected with a current source having a value of a fraction of −1 (inverse polarity) of the controlling value. The maximum intensity of the electric excitation field associated with this stimulation channel should be restricted to allow a controlled overlap between the maximum excitation fields associated with nearby stimulation channels while under this condition the amount of neural activation should be of the same strength (obviously depending on neural survival, etc.).

A stimulation channel is addressed by only one controlling value (stimulation amplitude) derived from one audio channel, which is used to determine the intensity and duration of the injected currents at the different contacts involved in this stimulation channel.

Each stimulation channel possesses its stimulation waveform pattern and waveform duration or time period. This waveform controls the instantaneous values of the current sources and or voltage sources associated with the contacts belonging to a stimulation channel. For example to obtain the instantaneous source values for the individual contacts of a stimulation channel, the controlling value of this stimulation channel is multiplied with the instantaneous value of the normalised waveform (max value is 1).

While stimulating the average injected current through each contact surface of the electrode should go to zero over time. One way to obtain this is by selecting charge-balanced waveforms. In case of charge unbalanced waveforms, like single monophasic pulse, the output signal from the audio channel should be a pure AC signal. If in this case the audio channel output contains a dc component, compensating cycle should be inserted to balance net charge to zero over time.

Figure 7:
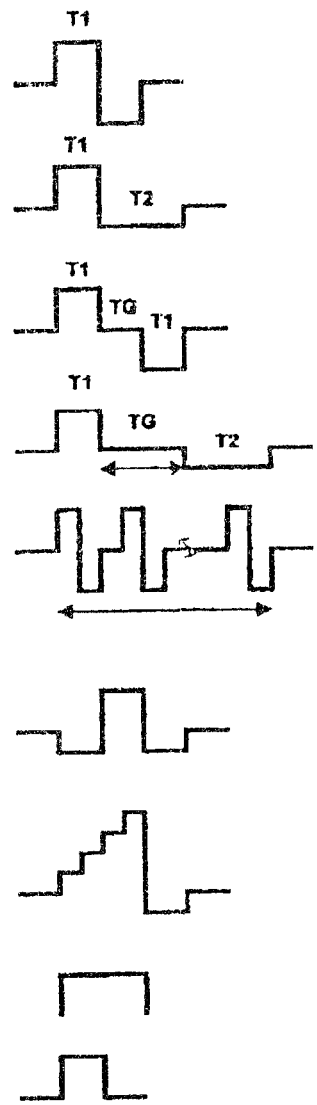
FIG. 7 shows examples of various waveforms used for stimulation.

Any waveform is possible. Each waveform is characterised by its shape and time pattern. FIG. 7 shows different shapes such as: a symmetric biphasic pulse (a), an asymmetric biphasic pulse (b), a symmetric biphasic pulse with a time interval (c), and an asymmetric biphasic pulse with a time interval (d), etc. For a variety of reasons, each stimulation channel can have a different waveform and waveform timing. For example, the asymmetric pulse can be used to improve the selectivity of bipolar stimulation in one stimulation channel when a charged balanced waveform with time gab can be used to avoid blocking the action potentials in another channel, etc.

When a stimulation channel is stimulating it will trigger action potentials in a group of nerve fibres. The initialisation place of those action potentials is called the excitation area. Increasing the stimulation level, most of the time, results in an increase of this excitation area. The intensity could be so large that the excitation field covers nearly all-accessible auditory nerve fibres. In this case introducing more stimulation channels has hardly any use. As a result the spread of excitation field should be limited. The excitation field obtained by stimulating this channel with its maximum value is called activation zone of the stimulation channel. The activation zone doesn't show necessary one monotonic spatial distribution. A stimulation channel should only have access to a population of nerve fibres that do not or only partially overlap with the activation zones of the adjacent (or other) channels.

The maximum control intensity, associated with a stimulation channel, can be derived from the allowed amount of overlap (for example 30%) between the activation zones of this channel and adjacent channels while they all stimulate approximately an equal amount of fibres (if accessible).

The criterion of reaching the most comfortable level (MCL) (=subjective sensation and interpretation) obtained by increasing the stimulation value of one stimulation channel up to the MCL can't be used as such to determine the maximum stimulation value for one stimulation channel.

As more and more channels become involved in cochlear implants, the MCL for a sound signal will be depending on the combined stimulation of more stimulation channels, which are activated by more audio channels having acceptable and controllable non linear overlapping filters. The relation between the maximal stimulation values for the stimulation channel, deducted from single channel stimulation to reach the MCL, and the maximum values derived from matching the MCL sensation during stimulation when sound signals, given at 60dBSPL (MCL), are passing through the signal processor, becomes more and more obscure. The way the signal processor and waveform generator handle the incoming signal primarily determines the MCL level for sound signals passing through the signal processor.

The mode of operation described here, associating different nerve fibres population (of nearly equal weight) to different stimulation channels with predefined overlap between activation area's, makes it possible to determine the maximum allowable stimulation intensity per channel.

The number of nerve fibres firing an action potential depends on the electric field distribution, the field strength variations, and the condition of the fibres with regards to the membrane noise, the inter-threshold variations, and the stimulation history.

When a fibre has fired an action potential, it enters a state in which it is temporarily non-stimulable absolute refractory period between 300 and 500 $\mu s$ (hereafter called refractory period). After this period, the stimulation threshold, changes during a period of 1 to 3 msec, from an increased value back to the original threshold value. This is called the relative refractory period. This relative refractory period is the result of, among other things, the residual opening of the $K^+$ channels and the is residual inactivation of the $Na^+$ channels.

It is very difficult and almost impossible, to ascertain directly the number of fibres synchronously firing an action potential as a response on a single stimulating pulse. It is possible to indirectly measure a relative value related to the number of activated nerve fibres in the auditory nerve fibre bundle.

The voltage variation measured in the vicinity of the auditory nerve, caused by the almost simultaneous firing of action potentials as a response on stimulation, is a spatial average of these action potentials called Compound Action Potential (CAP). As a consequence the shape and amplitude of this CAP depends strongly on the 3D spatial relation between excitation places and recorder points as well as the individual initialisation sites of the action potentials. That is why the amplitude (or surface under the curve) can't be an absolute indicator for the number of fibres firing an action potential.

The amplitude of the CAP (or surface under curve) is a first order relative value for the number of fibres being stimulated. The number of triggered fibres is related to the stimulation intensity, stimulation history and the individual thresholds of the fibres at that moment. The function relating the strength of the CAP response (amplitude or integrated surface) as a function of the stimulation intensity of a stimulation channel is called the growth function or I/O function. The growth function gives an indication on how the number of recruited fibres increases with the stimulation intensity.

Regularly a discontinuity can be observed in the slope of the I/O functions. This cannot be explained by the random distribution of the threshold value of the nerve fibres within the excitation field, but is probably related to a discontinuity in the localisation of the initialisation of the action potentials caused by the position of the various nerve fibre structures.

Low field strengths mainly activate the peripheral endings of the nerves (for example: the dendrites, Ganglion cells (cell bodies) or axons) and lead to the linear increase of the CAP amplitude. Higher field strengths trigger the axons of the auditory nerve fibre localised in the center of the modiolus. In this bundle, the nerve fibres of higher cochlear turns or adjacent zones lie very close together (especially in the upper turns), so that a small increase in field distribution can result in an enormous increase in the firing of action potentials. This could explain the discontinuity of the I/O function. The stimulation of nerve fibres emerging from higher turns (translated perceptually in lower frequencies pitch sensation) when stimulating channels in lower turns is called cross stimulation or cross talk.

Such cross stimulations must be avoided at all times. In low-frequency channels there is a high risk of cross talk with opposite areas in the same turn, since the neural structures lay very close together in higher turns.

The fact that a stimulated fibre cannot be activated again during the absolute refractory period makes it possible to determine the stimulation selectivity of electrodes (see Liang D. H. Kovacs, Storment and R. L. White 1991 IEEE Trans Biom. Eng. Vol. 38, pp.443–449). This feature can be used in the field of cochlear implants to determine relative overlap of activation zones by means of tuning-curves associated with the stimulation channels (see the European TIDE application NR1230 Jan. 8, 1995 Project manager Stefaan Peeters and description method and results of tuning curves for electrical stimulation with cochlear implants see Tide DEL231 of Aug. 6, 1997 Houben Schuylenbergh, S. Peeters)

The maximum allowable current in a stimulation channel is determined in such a manner that the activation zone of this stimulation channel only partially overlaps the activation zones (of equal weight) generated by adjacent channels. If a stimulation channel is responsible for cross stimulation the channel should be reconfigured.

As an example a method for deducting a maximal stimulation intensity of a stimulation channel is described. The method described is an objective method and can be used for the computerised determination of maximal stimulation level associated with a stimulating channel. There are also subjective methods, which requires the active involvement of the patients. The problem with those methods is that they cannot be used with small children and is very time-consuming.

The proposed method is based on the following reasoning: when channel n is stimulated with a minimum intensity sufficient to detect any CAP response triggered by a pulse (of any waveform) than the detection of a CAP means that this stimulation intensity allows recruiting a few nerve fibres. The amount of fibres recruited under this condition depends on the sensitivity and S/N (signal to noise ratio) of the measuring circuit. Those fibres are the first fibres, which are activatable by means of channel n. In case of poor nerve survival it is quite possible that the same group of excited fibres are also those fibres initiated first by another channel.

The low intensity stimulating pulse, which creates a minimal detectable CAP is called the probe pulse ($l_p^n$). When those fibres were activated a short time before (within the refractory period of those nerves) this probe pulse has been delivered, those fibres don't show a CAP response triggered by the probe pulse because most of them will be in the refractory period. Based on this feature the spread of excitation of other stimulation channels can be deduced. If other channels are stimulated with a high intensity pulse before the probe pulse is delivered, the spread of excitation could be so large that also the fibres normally activated by the probe pulse are excited. The response to the probe pulse is suppressed or masked by the pulse in the other channel. This pulse is called the masker. The proposed method according to the invention to determine a maximal stimulation level for each stimulation channel is based on this feature.

Suppose that a probe pulse is placed in stimulation channel n+1. Channel n is stimulated with a masker pulse 300 to 500 usec before the probe pulse. The intensity (In) of stimulation channel n is increased so that the CAP response on the probe signal delivered by stimulation channel n+1 is reduced. At this moment the spread of excitation field of stimulation channel n in the (apical) direction of channel n+1 is so large that it interferes with the nerves normally responding on the probe signal in stimulation channel n+1. The value $I_n^{n+1}$ is the level of intensity in channel n just enough to mask partially the response in channel n+1. To deduct the spread of channel n in the basal direction a probe signal can be placed in channel n−1 and again a masker in channel n. This results in a value of $I_n^{n-1}$ which is the level of intensity in stimulation channel n just enough to mask partially the response of stimulation channel n−1.

For the maximum stimulation value associated with stimulation channel n it is preferable to take the minimum of $(I_n^{n+1}, I_n^{n-1})$.

The procedure described above is repeated for each of the N stimulation channels. In case of the first and last channel $I_n^{n+1}$ or $I_n^{n-1}$ doesn't exist.

To check cross stimulation determine the $I_{max}^n$ for all channels and then check consecutive whether any cross stimulations occurs with any other stimulation channel when stimulating with the maximum values and using the same method. If cross stimulation occur, reconfigure the responsible stimulation channel.

If a stimulation channel's $I_{max}^n/I_p^n$ ratio is very small relative to the values for adjacent channels, this could be again a reason to reconfigure this channel.

A stimulation channel n is thus basically determined by three parameters:
1) the surface-contact configuration. This is the combination of different contacts grounded or connected with current or voltage sources controlled by amplitude values derived from the input value of the stimulation channel ($A_{in}^n$) and modulated by the waveform. Contacts with abnormal impedance values (for example wire breaking) are no candidates for the channel configurations;
2) the waveform pattern and waveform duration.
3) the maximum allowable control intensity, which limits the spread of the associated activation field along the nerve fibre population. This limitation is determined by the allowable overlap between (±equal weight) activation fields from adjacent. This value indicates a maximum field strength for the considered stimulation channel.

These parameters are patient-related and are dependent on: the position of the electrode in relation to the nerve fibre structures (dendrites, cell body and axons), the location of surviving excitable nerve fibres, the tissue reaction round the electrode (which could influence the electrical field distribution), the insertion depth of the electrode, etc. Since these parameters are patient-dependent and can change from stimulation channel to stimulation channel, they are determined for each patient and channel.

Once the stimulation channel is defined, other parameters can be measured and assigned to the stimulation channel:
a) the minimum intensity (current or voltage) needed to stimulate a few nerve fibres or just not to stimulate a few nerve fibres ($I_{offset}$);
b) the parameters describing the voltage distribution along all the contacts of the electrode array while stimulating this channel with his corresponding maximal level. Those parameters are not necessary symmetrical for contacts situated apical or basal from the stimulating contacts and depends on the stimulation configuration. For example monopolar stimulation can show more asymmetry between parameters then transversal stimulation. The parameters include the extrapolated voltages under the stimulating contacts, which are responsible for the voltage distribution along the electrode array. Those parameters are stored as a first and second identifier, identifying a field spread in a basal and apical direction relative to a position of the electrode contacts of the considered stimulation channel.

All these parameters are stored in a memory element of a stimulation channel configuration unit 29 connected with the storage buffer 24 and the wave pattern generator. The channel configuration unit is provided for defining the stimulation channels i.e. for storing the channels determined as described here before. In the channel configuration unit at least two electrode contacts are allocated to each stimulation channel. The waveform pattern and duration for each channel are stored in the waveform generator 25 connected with unit 29.

The choice of useful channel configurations based on contact configuration, waveform and waveform duration, is influenced by the minimum current ($I_{offset}$) and the achieved relative dynamic range ((Imax-Imin)/Imin). Imax limits this dynamic range, which is on his turn related to the restricted overlap between stimulation channels. As a consequence the more channels the lower Imax. With other words the preferable dynamic range is also a function of the amount of stimulation channels involved. Preference is given first to low thresholds and secondly high relative dynamic ranges.

Figure 8:
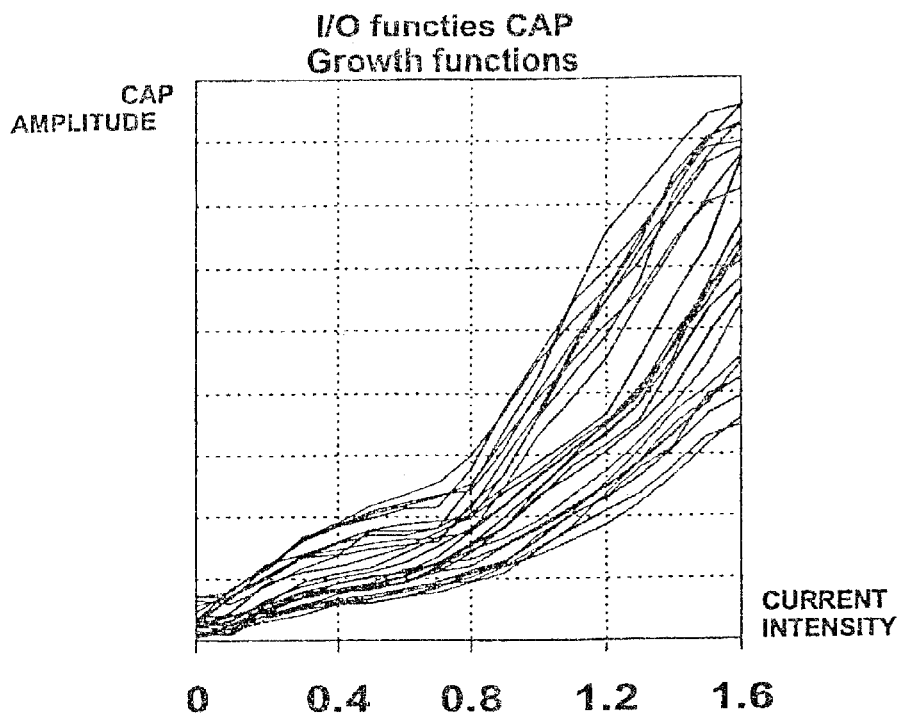
FIG. 8 shows examples of CAP I/O functions for different stimulation channels.
Figure 9:
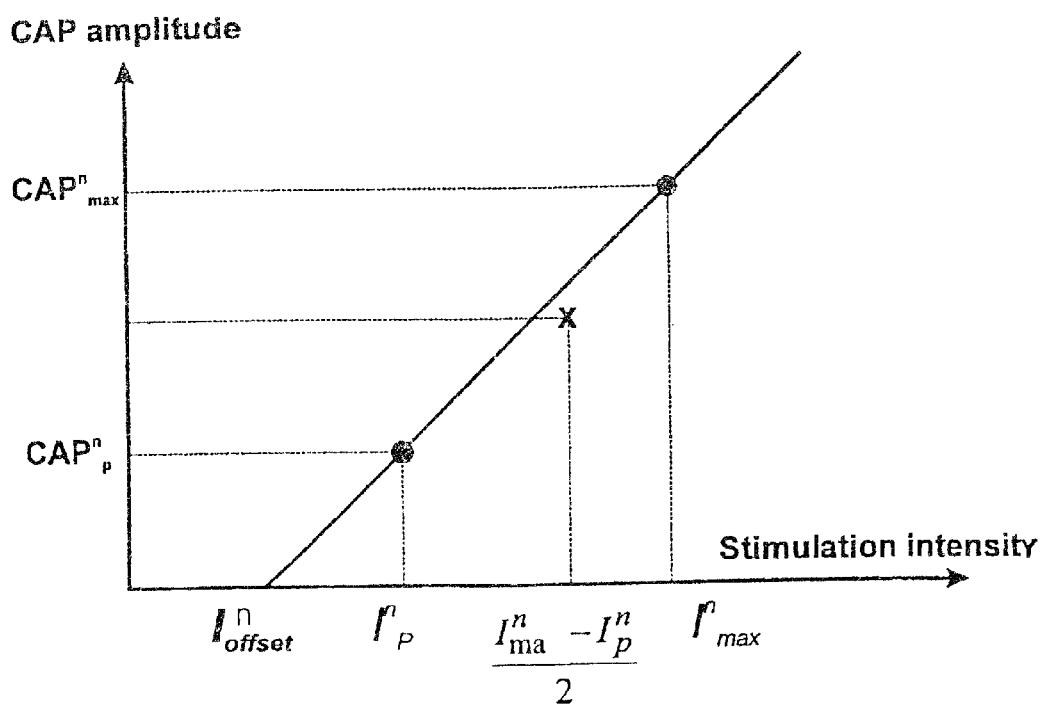
FIG. 9 shows an example of interpolation to obtain Imin.

The minimum current $I_{offset}$ necessary to stimulate just a few nerve fibres with a stimulating channel can be deduced as follows:
for weak stimulating intensities, the increase in CAP can be regarded as linear. FIG. 8 gives an example of the relationship between the stimulation intensity and the CAP amplitude response for different channels.
The minimum intensity can be deducted by means of interpolation as illustrated in FIG. 9.
For example a linear interpolation results in:
$I_{offset}^n = (C_{max}^n I_p^n - C_p^n I_{max}^n)/(C_{max}^n - C_p^n)$,
where $C_{max}^n$ respectively $C_p^n$ represent the CAP amplitude.
Inserting a control CAP measurement for an intensity corresponding to $(I_{max}^n + I_p^n)/2$ allows $I_{offset}$ to be determined more accurately.

The dynamic range in a stimulation channel is determined on the one hand by the minimum amplitude ($I_{offset}$), which did or did not cause action potentials in a small subpopulation of the activation zone, and on the other hand by the maximum stimulation amplitude ($I_{max}$) in that stimulation channel.

The dynamic range can be expressed as $Dyn = (I_{max} - I_{offset})/I_{offset}$. The dynamic range depends on Imax, which is dependable on the number of stimulation channels.

Or Dynlog=20 log Dyn, which vary between 1 to 26 dB.

During simultaneous stimulation of channels, the electrical fields of different stimulation channels interact at the level of cochlea due to the conductive features of the medium as for example the electrolytic fluid filled spaces. The overall electric field distribution during simultaneous stimulation differs from the sum of the individual field patterns of the same stimulation channels obtained during non-simultaneous stimulation. As a result a subgroup of fibres associated with a stimulation channel is modified depending on simultaneous or not simultaneous stimulation.

A method is now described on how the stimulation strategy can cope with this problem so that the population of resulting activated nerve fibres during simultaneous stimulation matches as much as possible to sum of the populations of activated nerve fibres if all channels involved are stimulated non-simultaneously.

Figure 10:
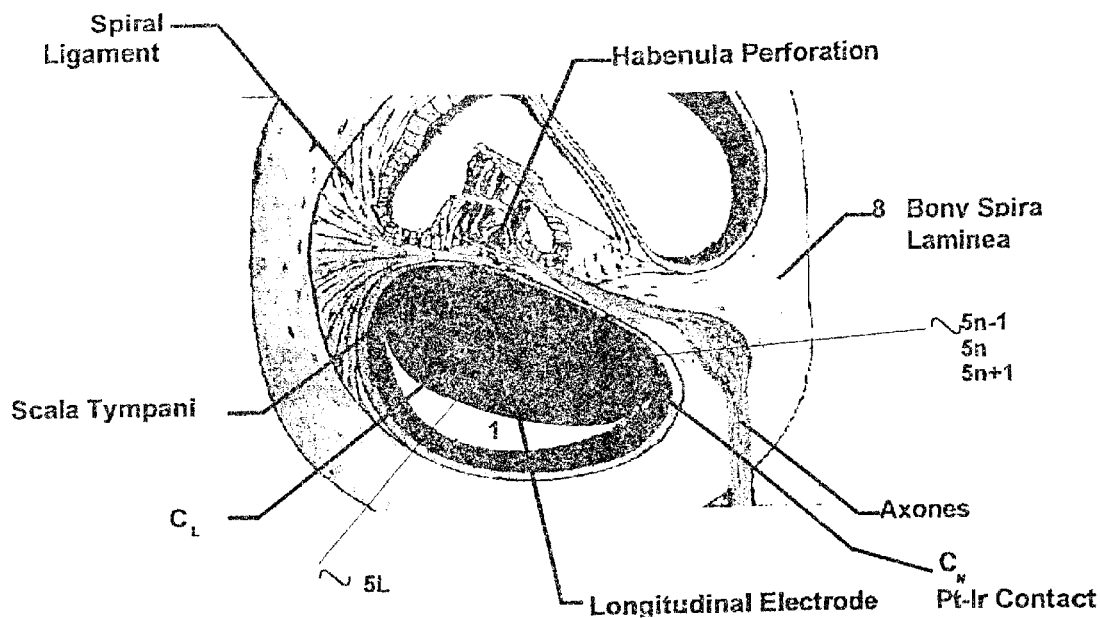
FIG. 10 shows a cross section showing an example of the position of a multichannel electrode in the scala tympani.

FIG. 10 shows the position of the cross section of a multi-channel electrode in the Scala Tympani. In this example the electrode consists of a silicone substratum with high electrical resistance and individual contacts $5^{n-1}$, 5n, 5n+1, and a common longitudinal electrode 5L. When a current is sent from contact $5_n$ to the longitudinal electrode 5L, it flows from bony structure through the nerve fibre and along the bony structure 8 back to the longitudinal electrode. The current path has also a longitudinal component. The three-dimensional, non-homogeneous conductive medium is represented schematically in FIG. 11 as a first order approach based on a simplied resistance model. This model is sufficient to clarify the reasoning and terminology.

Figure 11:
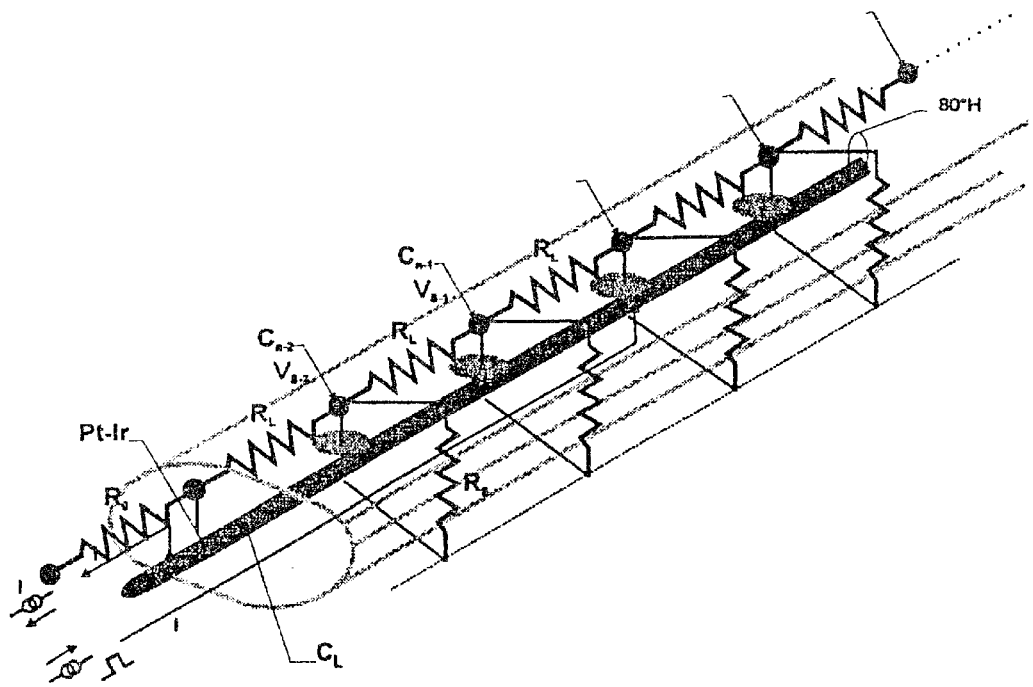
FIG. 11 shows first order approximation of the current paths from contacts to a longitudinal reference electrode.

FIG. 11 shows the conduction path of the longitudinal component presented by the resistance $R_L$ and the conduction path, through and along the nerve fibres, presented by $R_S$. Ro is a representation of the low resistance path to outside placed contacts. All $R_s$ resistances are connected to the longitudinal electrode and there form an equipotential line. Rs includes the interface impedance of the longitudinal electrode.

When a current I is sent between contacts $5n$ and $5_L$, the current has to flow as much as possible along the fibres in the vicinity of contact $5n$ and thus cause high voltage gradients along the fibres. Preferably the longitudinal current spread along the electrode is as small as possible. Therefore, the resistance of the longitudinal current-path should be high in respect to the current path resistance towards the longitudinal electrode.

If $R_L$ is much larger than $R_s$, most of the current will flow through $R_s$ and the stimulation will be very selective. If $R_L$ is much smaller than $R_s$, a large current will flow in longitudinal direction, creating higher voltages along the electrode. For other stimulation configuration total different behaviour can be expected.

Those voltages can be recorded with the implant thanks to incorporated high input impedance amplifiers connectable to the contacts, $5n+1$, $5n+2$, etc., Those voltages can be recorded with the implant thanks to incorporated high input impedance amplifiers connectable to the contacts, $5n+1$, $5n+2$, etc.

Figure 12:
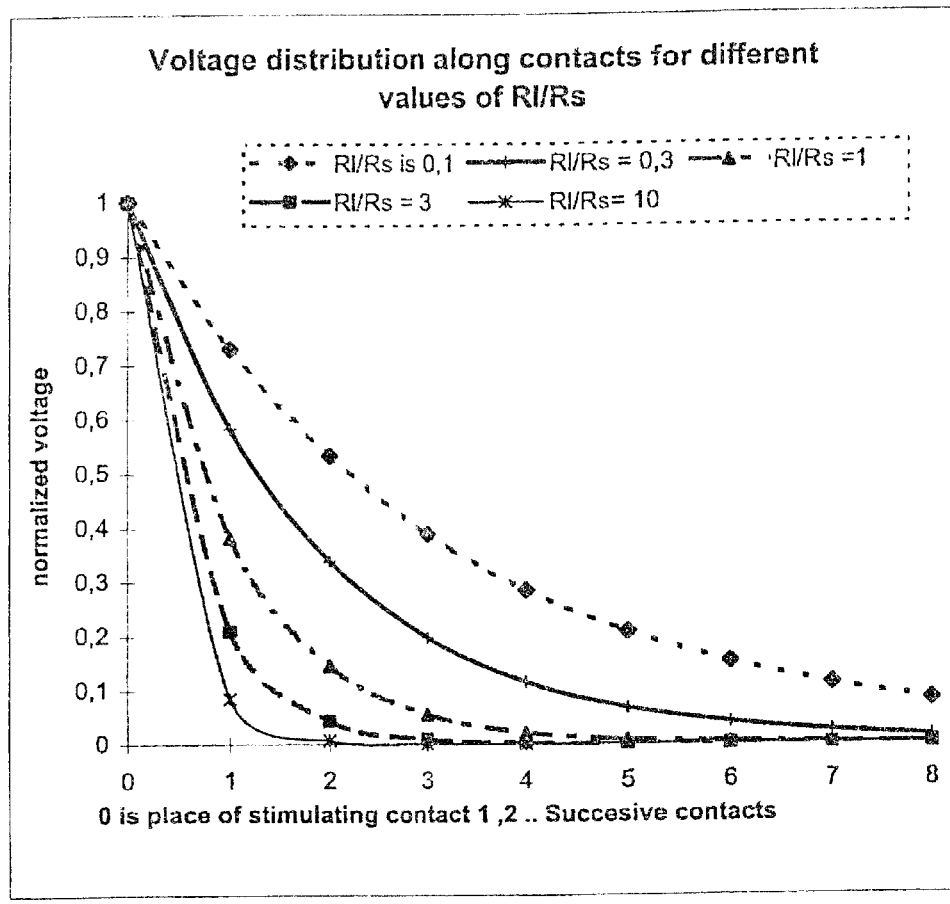
FIG. 12 shows Voltage distribution across electrode evoked by a stimulating contact.

Considering a simplified model, the voltage distribution along the contacts $5_1 \ldots 5_n$ is determined by the $R_L/R_S$ ratio as illustrated in FIG. 12.

This figure shows five curves (for different $R_L/R_s$ ratio) as a function of distance relative to the stimulating contact. The contacts shown are those localised in the apical direction of the stimulating contact $5n$. 0 is place of the stimulating contact, 1 is contact $5n+1$ etc.

In case of transversal stimulation the model gives, as a first approximation, a symmetrical result. If stimulating towards an outside contact then the curve could be highly asymmetrical due to different current paths in apical and basal direction.

The curves are normalised so that the voltage $V^n_s$ below stimulation contact $5n+0$ is equal to 1 Volt.

It can be observed that when RLURS is high, the current spread is low and interaction during simultaneous stimulation will be low. When RI/Rs is low the current spread is high.

For the model, the ratio between the voltages of adjacent contacts is determined by: with $K=R_L/R_S$ $$\frac{V_p}{V_{p-1}} = \frac{1}{\left(1 - K + \frac{2}{(1+\sqrt{1+4/K})}\right)}$$

p is the location of a contact point en p−1 an adjacent contact. The voltage drop along the electrode follows an exponential curve of the form:

$$V = V_s \exp(-x/d) \text{ with } d = \frac{1}{\ln\left(1 + K + \frac{2}{(1+\sqrt{1+4/K})}\right)}$$

$V_s$ is connected to $I_{max}$ by $V_s = R_{int} * I_{max}$, $R_{int}$ being a proportionality factor.

d=decay parameter and x is the number of contact places in respect to the stimulation place.

The decay parameter can be derived from internal measurements.

By measuring the voltage differences between electrodes contacts during stimulation and sending this information out again, it is possible to ascertain the voltage Vs and the decay value d by means of curve fitting. It is preferable to register differentially to improve the S/N because the internal voltages are quit low.

In the previous model an example of a transverse stimulation method was given, in which all channels use a common contact, the longitudinal electrode. This can be generalised for all stimulation configurations.

In the previous model it was assumed that the longitudinal and radial resistance paths are identical. In reality this is not the case. There can be a big difference between the basal region and the apical region. Therefore it is always necessary to perform a separate curve fitting for both the basal measured data points and the apical data points in relation to the stimulation contacts. This gives a decay that is constant in the basal direction and one in the apical direction. In such a manner the first and second identifier which identify the field spread in basal and apical direction are determined.

The purpose of the automatic registration of the decay constants d and the interpolated internal control voltages at maximal stimulation intensity of the stimulation channel is to enable to correct the stimulation intensity during simultaneous stimulation and select stimulation channels which can be grouped together for simultaneous stimulation.

Figure 13:
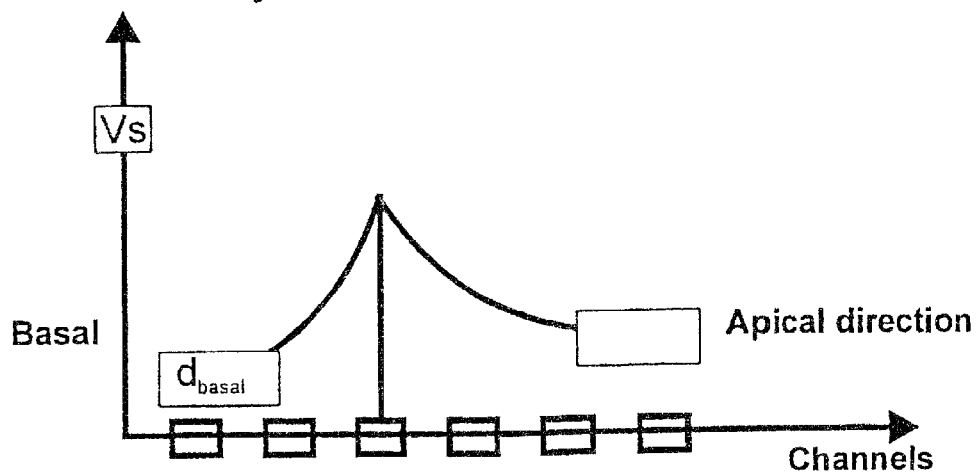
FIG. 13 shows different voltage variations behaviour along the channels in apical or basal direction.

FIG. 13 shows a schematic course of voltage variations along the electrode when, for example, stimulation channel P is activated with a current I producing a driving voltage $V_S$. There are two different decay contacts in this example.

Figure 14:
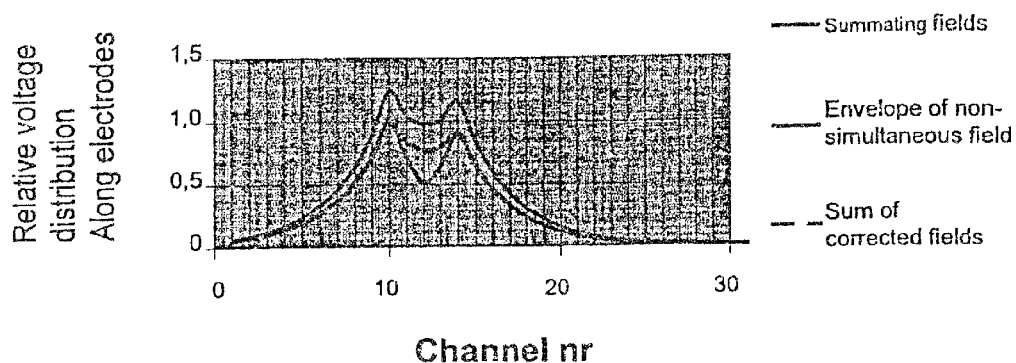
FIG. 14 shows the effect of simultaneous stimulation on the field distribution for channels with high current spread.

While two channels are stimulated simultaneously the corresponding fields interact. This can vary between addition and subtraction depending on phase relations between stimulating pulses. As a consequence, field gradients near the nerve fibres are modified. FIG. 14 shows the voltage distribution result, from the model with a large decay parameter 3, when stimulating two channels simultaneous or not. In this example, channel ten and fourteen are stimulated in phase.

The lowest curve represents the envelope of the two distributions when stimulated sequentially in time and as such don't interfere.

Figure 15:
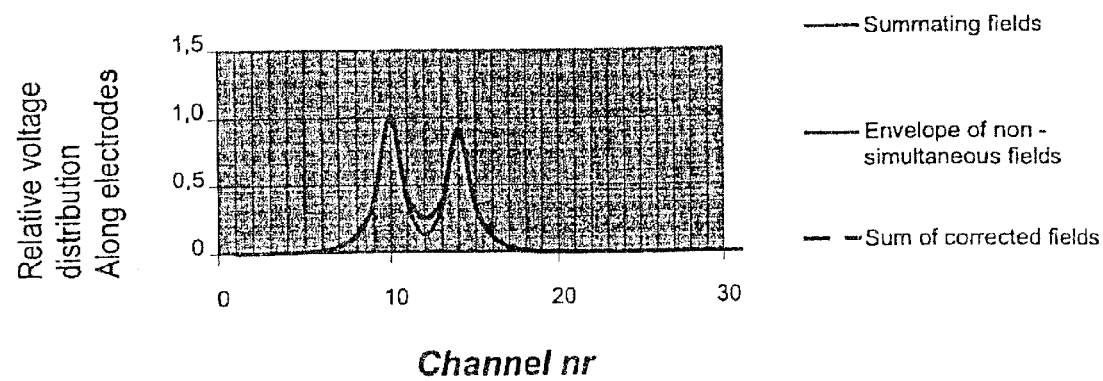
FIG. 15 shows the effect of simultaneous stimulation on the field distribution for channels with low current spread.

In FIG. 14, the highest curve represents the voltage distribution in the model along the contacts when stimulated simultaneously. As can be seen, peak values related to the places of channel ten and fourteen are increased due to interaction. This should be avoided as it perturbs the stimulation and consequently the audible result. Also, the voltage distribution between the peaks is increased which could result (also depending on field gradient changes) in stimulating nerve fibres allocated to in between channels. During simultaneous stimulation the increase of the field strength around the peaks of channel ten and fourteen can be cancelled by reducing the input stimulation levels of channel ten and fourteen taking in account the decay parameters. The result is shown in FIG. 14 by the dotted line. The peak now matches the envelope of the non-simultaneous fields. The area between the peaks is still showing higher voltages compared with the non-simultaneous envelope. This means that interaction effect is not fully compensable and that due to interaction the field strength between channels could surpass the firing threshold of in between fibres. This is especially the case when the decay parameter is high. To less this effect, the simultaneous stimulated channels must be further apart. If the decay parameter is low (d=1) as illustrated in FIG. 15. The interaction can be fully compensated by adjust the input intensity (if necessary) of the stimulating channels.

Table 1 gives a first order relation between the internally measured decay value and the minimal contact distance along electrodes for channels, which can be activated simultaneous (with or without input compensation).

The first and second column give the limits for d (d is average ($\bar{d}$) d of the first channel and d of the other channel in the other direction). The third column gives the distance between the simultaneous stimulating stimulation channels in terms of number of contacts (#) between the nearest associated contacts of both channels.

Table 1

| Decay parameter | $\bar{d}$ | # |
| --- | --- | --- |
|  | .3 | +2 |
| .3 | .8 | +3 |
| .8 | 1.5 | +4 |
| 1.5 | 2.5 | +5 |
| 2.5 | 4 | +6 |
| 4 | 5.7 | +7 |
| 5.7 | 8.5 | +8 |
| 8.5 | 10 | +9 |

For example when the average decay value is between 2.5 and 4, the two channels must be 6 or more contacts apart for simultaneous stimulation. In order to stimulate simultaneously two channels two contact apart, the decay factor needs to be <.3.

Consequently, this table limits the choice of channels that can be stimulated simultaneously. The decay value depends strongly on the localisation of the electrode. Increasing RL is obtained by reducing the volume of low conductive electrolytic fluid between the contacts. Placing contacts as near as possible towards the basilar membrane or inner wall can do this.

An other consequence of the voltage spread is observed when a channel q has to be stimulated with an intensity evoking a driving voltage of $V_s^q$, and this driving voltage value is lower than the local voltage caused by stimulating channel p with $I_p$. In this case the stimulation of this channel q has to be skipped. If the local voltage is lower, stimulation occurs, if necessary with a corrected value, so that the ultimate composed voltage distribution along the electrode matches as much as possible the envelop of the individual voltage distributions. This can be achieved by solving p equations with p unknowns if p channels are stimulated simultaneously.

The stimulation strategy can incorporate a so-called "neural repair" function that takes into account the nerve fibres absolute and relative refractory period.

Figure 16:
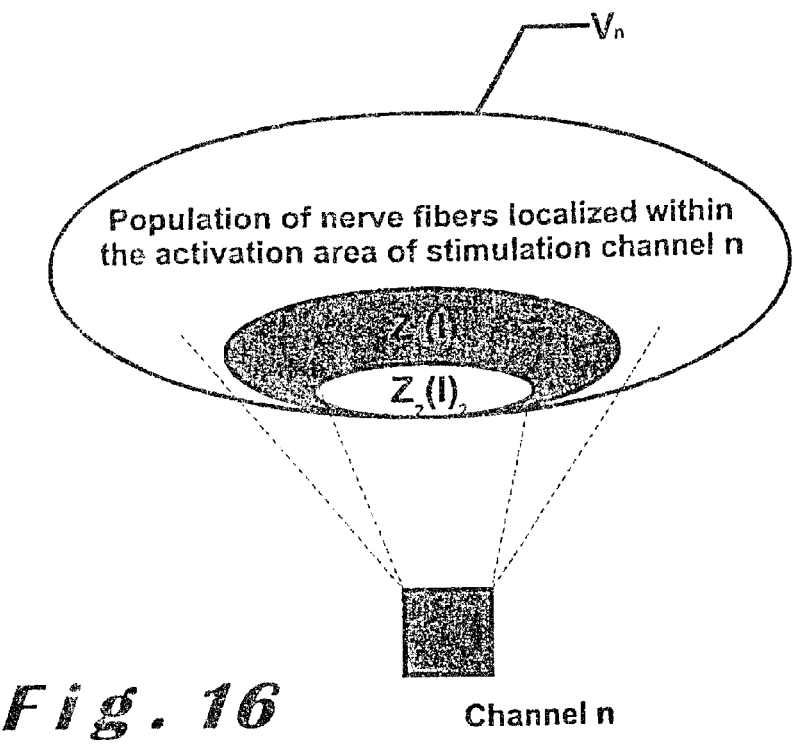
FIG. 16 shows a schematic representation of the stimulation zones based on different stimulation intensities n. $V_n$ representing the set of fibres of the activation zone of a stimulation channel n

In FIG. 16, the channel n has an activation zone represented by the set $V_n$, in accordance with the intensity $I''_{max}$. At the point in time T1, the channel n is stimulated with amplitude I1. The corresponding recruitment zone is represented by Z1. Due to the stochastic threshold variations (due to membrane noise) of the nerve fibres in time, not all fibres in zone Z1 will fire an action potential. Those fibres situated in the center of the excitation zone will usually be activated, since the voltage fields there greatly exceed the threshold values at that location. The fibres situated on the edge of the excitation zone, where the field strengths are smaller, shall be activated less percentage-wise, because the threshold fluctuations have there a relatively strong influence.

If the next stimulation amplitude in channel n at moment T2 is larger than the previous one, nerve fibres from a larger excitation zone Z will be recruited. In this case the stimulation channel is activated.

If the amplitude is smaller than the previous pulse at T1, the recruitment zone is smaller (see Z2) and is situated in the recruitment zone Z1. The fibres in this zone are to a large extent activated by the previous pulse. In other words, they are in their absolute or relative refractory period, dependent on the time difference between T1 and T2. If the stimulus interval T2–T1 is smaller than the absolute refractory period $T_{AR}$, the number of fibres reacting to the stimulus will be relatively small. In this case the pulse does not stimulate.

Figure 17:
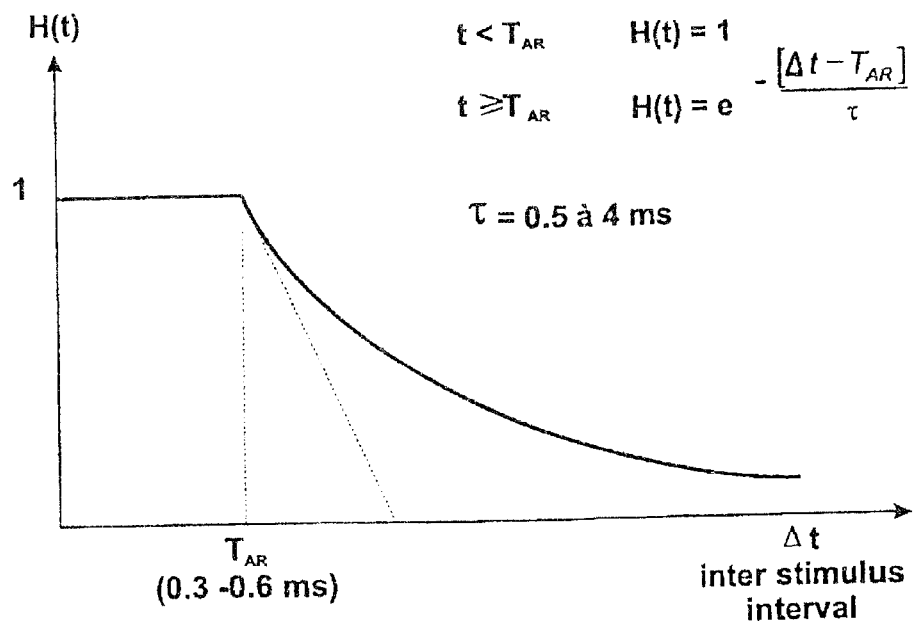
FIG. 17 shows a representation of the Neural-Repair function.

To take this feature in account during stimulation a neual-repair function H ($\Delta$t) is introduced as shown in FIG. 17, with $\Delta$t being the inter-stimulus time. The value of the function for a stimulation interval smaller than $T_{AR}$ is equal to 1. Subsequently the function drops over a period of 0.5 to 3 ms. The illustrated function is an exponential decaying curve for stimulus interval time $\Delta$t higher than>Tar. For example: $\exp^{-(\Delta t - Tar)/\tau}$.

The parameter $\tau$ is a channel-programmable time constant with a value between 0.5 and a few (e.g. 3) ms When the incoming amplitude for a stimulation channel is higher than the previous one, it is accepted for stimulation. When the incoming amplitude is higher than the previous value multiplied by the neural-repair function H ($\Delta$t), than this new value is. used for stimulation.

A true representation of the sound at the neural level requires an electrical stimulation that accurately follows the spectro-temporal characteristics of the sound. In order to transfer the temporal characteristics, such as "phase information", to the nerve fibres, it is necessary to activate the stimulation channels sufficiently fast.

The stimulation strategy can select two extreme situations for sending the information to the nerve fibres. All stimulation channels are activated successively and this is repeated cyclically. This is known as the Continuous Interleaved Strategy (CIS). Or all channels are stimulated simultaneously, and this is repeated, an example is SAS.

If channel interaction exists during simultaneous stimulation and compensation is required, it is important to use the same sampling-waveform and waveform timing for all simultaneous stimulated channels that show interaction, otherwise it is impossible to carry out field interaction corrections for them.

Figure 18A:
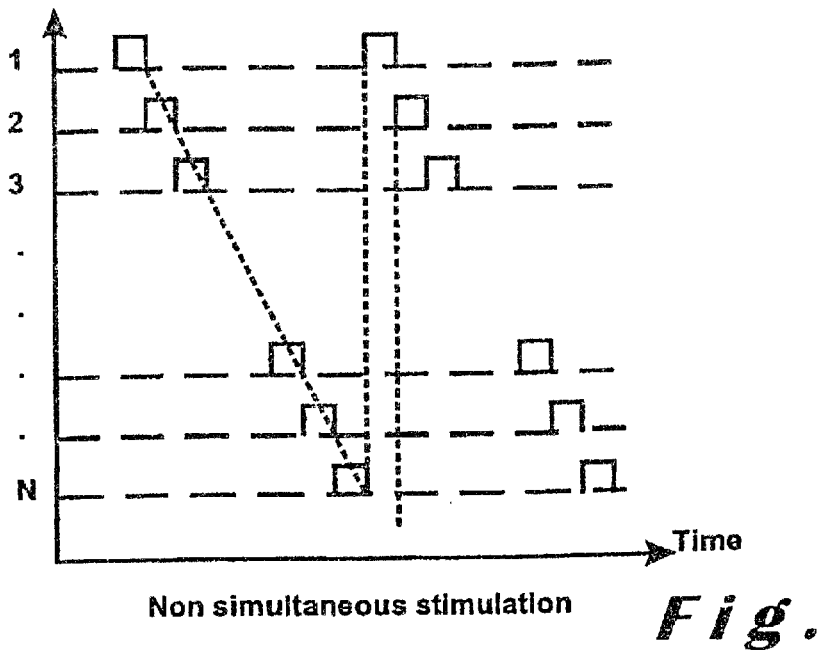
FIGS. 18a and 18b shows illustrations of simultaneous and non-simultaneous stimulation.
Figure 18B:
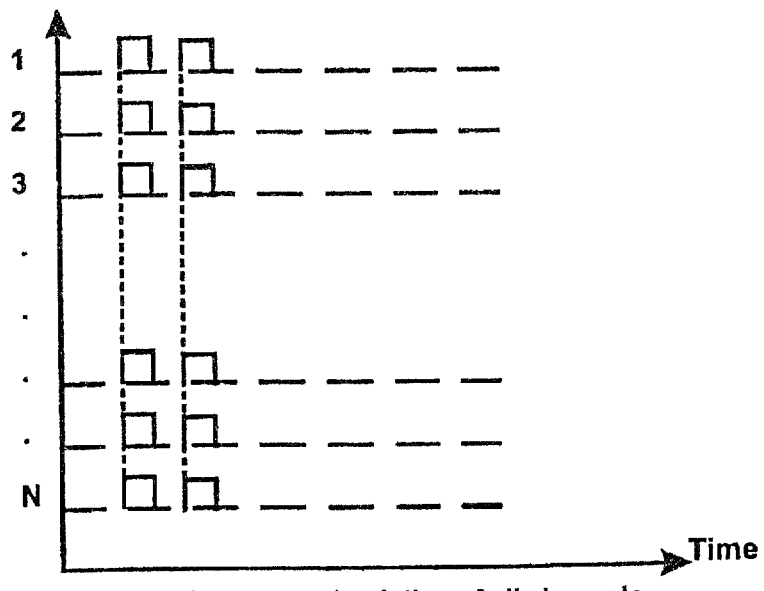

FIG. 18a illustrates a situation with non-simultaneous stimulation and FIG. 18b with simultaneous stimulation. The drawback of CIS is that the stimulation speed per channel decreases as the number of channels increases. For example, if the stimulation duration per pulse is 100 $\mu$s and the number of channels is 50, then the maximum stimulation frequency per channel will be 200 Hz. This is not compatible with the desire to achieve the highest possible stimulation speed per channel in order to carry over the temporal information in a sufficiently accurate manner.

In the case of simultaneous stimulation, it is worth mentioning that conflict situations can occur, e.g. one or more defined channels can use the same contact, although the waveforms and timing of the channels differ. An additional disadvantage is the risk of high power consumption peaks when all channels are activated simultaneously.

A compromise between CIS and total simultaneous stimulation is combining the channels in various groups. The stimulation channels put together in one group are stimulated simultaneously. All channels are divided once or more over different groups. The groups are stimulated sequentially one after the other. For this purpose the cochlear implant according to the present invention comprises an ordering unit provided to order groups of stimulation channels according to a sequence defining the order according to which the different groups are sequentially stimulated. The ordering unit comprises a group-stimulation sequence table representing which stimulation channels will be stimulated simultaneously and in which order the groups will be stimulated in. Table 2 shows an example.

TABLE 2

| Channel nr involved => | Group1 Time: ΔT1 | Group2 Time duration: ΔT2 | | Group q Time: ΔTq |
|---|---|---|---|---|
| Stim-chan1 | Yes | Yes | | Yes |
| Stim-chan2 | | | Yes | |
| Stim-chan3 | | | | Yes |
| Stim-chan4 | Yes | | | |
| Stim-chan n (n can be much larger than available contacts very large) | | Yes | Yes | |

The content of such a stimulation sequence table is saved in the waveform generator unit. During the first time interval ΔT1 group1 is stimulated composed of stimulation-channels 1, and 4 together (the waveform-timings of channel 1 and 4 are not necessary equal to the time duration of group1). During the next time interval ΔT2 channels of group 2 are stimulated ect. Group1, group2, etc. to group$_q$ are stimulated successively.

Criteria will now be provided on how to construct a group:
A group contains all possible stimulation channels with following restriction:
1) Channels in the same group cannot have common active contacts when this is detrimental to the electric field distribution of the channels during simultaneous stimulation. But permissible are e.g. channels with a common grounded contact.
2) Channels belonging to the same group and which are candidates for input compensation, to correct field interaction, must have the same waveform structure and waveform timing to allow for input compensation. Non-interacting channels can have their independent waveforms and waveform timing.
3) Channels belonging to the same group have no significant field interaction or if so the interaction should be compensable.
4) Channels belonging to the same group should have comparable $I_{offset}$ and dynamic ranges (less then factor 3 difference) If not it is preferable to place them in different groups.
5) Channels which have an uncompensable field interaction can't be placed in the same group.

It should be mentioned that a stimulation channel could belong to both group "a" and group "b", as long as it does not cause a conflict with the other channels in the group.

If a group is becoming too large (due to the physical limitations of the implant, such as excessive power peaks, etc.), it can be divided into 2 or more subgroups, which are then placed in time one after the other.

Each group has its own programmable duration, which is minimum as long as the maximum of any waveform duration of stimulation-channels belonging to this group. This collection of groups forms a cycle called stimulation sequence, and this cycle is repeated again and again.

The order of placing of the different groups in the cycle is such that the averaged time difference (calculated across the whole sequence) between the stimulation of adjacent channels is maximal to reduce temporal neural effects, which could result from the overlap of the excitation fields of adjacent channels.

An example of a procedure to build groups will now be given.
The following procedure can be used to form stimulation groups:
Arrange all stimulation channels starting from channel 1 that have no mutual conflict according to the previous criterion in a group;
In the second group, arrange the channels which do not belong to the first group, and which have no mutual conflict according to the criterion. Add to this group the channels of group 1 that have no conflict with channels of group 2;
In the third group, arrange the channels which do not belong to either group 1 or group 2, and which have no mutual conflict. Add to this group the channels of group 1 and group 2 that have no conflict with group 3;
Continue this way until for example only 5% of the channels have not been placed in a group. Check if other configurations of stimulation channels, stimulating equal neural regions can be fitted into the previous groups. If this is not possible, remove the remaining channels and re-determine $I_{max}$ for the adjacent channels;
If a group contains too many channels (limitations of the implant) that can be stimulated simultaneously, this group can be divided into subgroups, which are placed one after the other;
The choice and division of groups can be done by computer software. This is part of the automatic fitting.

The amplitude values in the storage buffer have to be transformed into stimulation intensities within the dynamic range of the stimulation channel.

Figure 19:
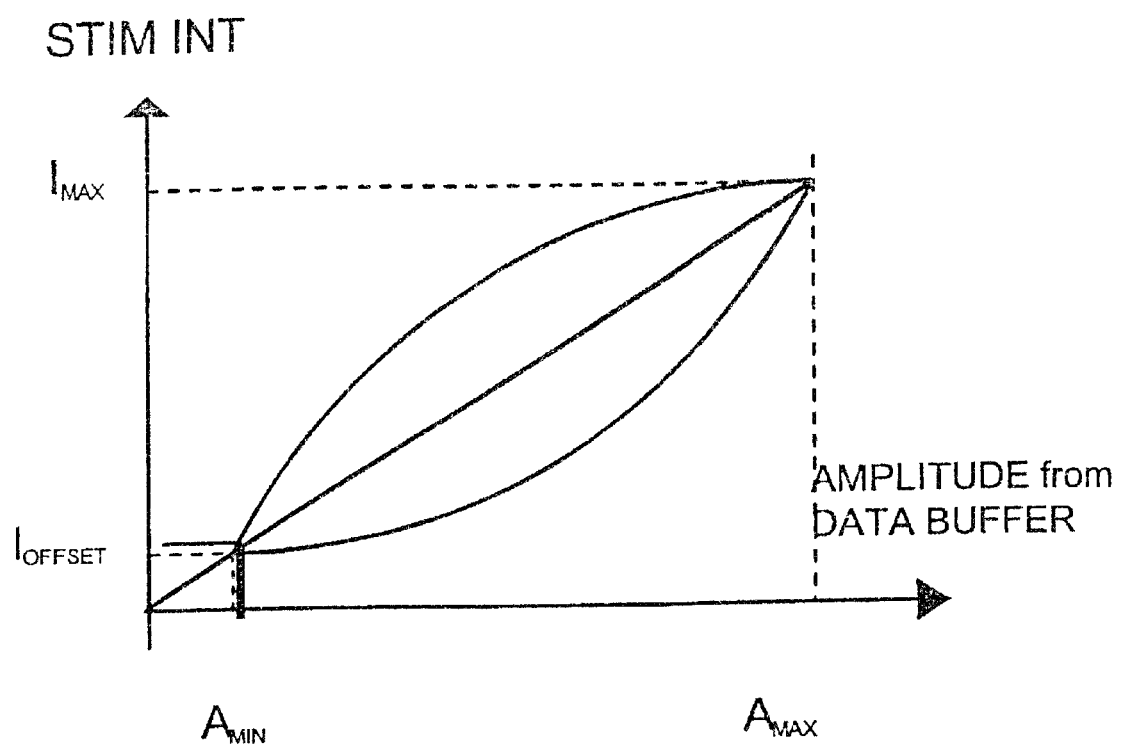
FIG. 19 shows an example of the conversion from amplitude value from data buffer to stimulation intensity for a stimulation channel.

For this reason each stimulation channel has its own conversion table or monotonic increasing conversion function, as shown in FIG. 19.

A is the amplitude value coming from the storage buffer. $A_{min}$ is a programmable amplitude value depending on the compression in the audio channel. $A_{max}$ is the maximum amplitude value. $I_{offset}$ and $I_{max}$ are the minimum and maximum current for this stimulation channel.

The maximum value in this audio channel (depending on the signal processor) is linked to $I_{max}$ of the stimulation channel. The function between A and I can have a linear relation, or can be linked by a compression or expansion curve.

An overview of the stimulation strategy will now be described.

Figure 20:
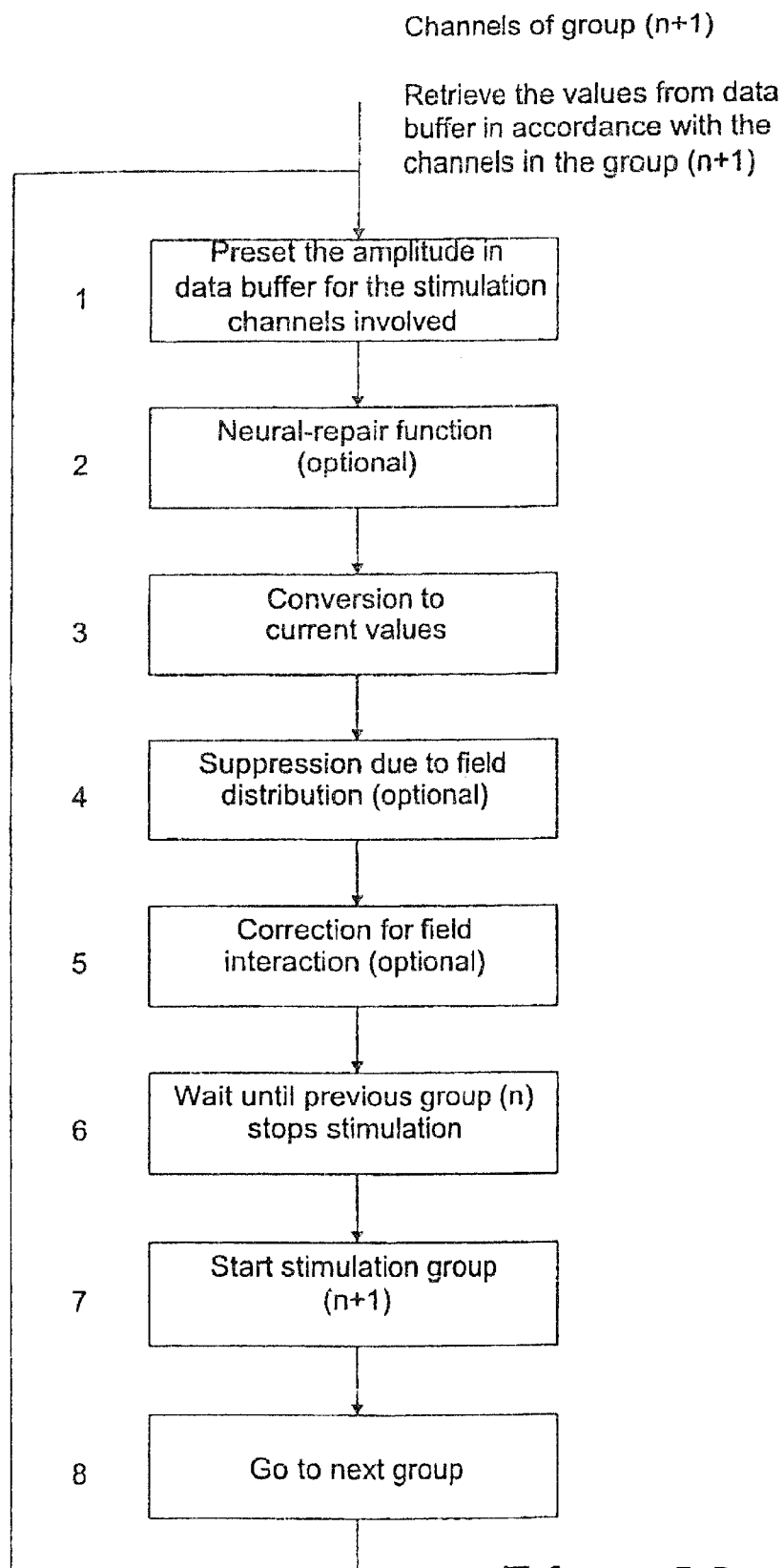
FIG. 20 shows an example of a stimulation cycle.

FIG. 20 shows an example of a flow diagram for stimulation, which is repeated successively.

When group N is stimulating, preparations are made for the stimulation of the next group N+1.

$1^{st}$ step

The amplitude values corresponding to the stimulation channels of group N+1 are retrieved from the storage buffer. For each channel the sampling unit belonging to the waveform generator controls the access to the data storage buffer at this moment. Channels with no access at this timing have a value zero. Channels with access read the value from the peak hold buffer and set the value in the data buffer to a preset value.

$2^{nd}$ step: Neural-repair function For each stimulation channel, the time of the previous stimulation is taken into account. The neural-repair function is implemented and programmable for each channel. If the new amplitude is smaller than the previous stimulation amplitude multiplied by the repair function, this channel will not be stimulated and the amplitude is set to zero. If all amplitudes of the stimulation channel are zero the sequence jumps to next group N+2. Go to $1^{st}$ step.

$3^{rd}$ step: transformation of audio channel outputs to stimulation intensities.

$4^{th}$ step: suppression by field distribution.

$5^{th}$ step: correction for field interaction $6^{th}$ step: wait until previous group n stops stimulation.

$7^{th}$ step: stimulate group n+1 according to the corresponding time patterns.

$8^{th}$ step: prepare next group.

What is claimed is:

1. A cochlear implant comprising a signal processor having a set of audio channel units and being provided for the conversion of sound signals, according to a frequency related tonotopic division, each audio channel being provided for applying a frequency related filtering to said sound signal, each audio channel having an output associated with a first sampling unit provided for sampling at an audio channel associated sampling rate the signal output by its associated audio channel unit and writing sampled signal values into a storage buffer, each sampling unit being connected with said storage buffer provided for temporarily storing said sampled signal values, said storage buffer being connected with a waveform generator comprising at least one stimulation channel, said waveform generator and said storage buffer being connected to a read signal generator provided for generating read signals enabling to read the stored sampled signal values from said storage buffer, said waveform generator being provided for retrieving under control of said read signal said sampled signal values of each audio channel from said storage buffer and for generating based on said sampled signal values waveforms having a time period and a wave pattern, said waveform generator being provided for stimulating by means of said waveforms electrode contacts of said cochlear implant, characterised in that said read signal generator is provided for generating said read signals asynchronously from said writing into said storage buffer.

2. A cochlear implant as claimed in claim 1, characterised in that said storage buffer is provided to set a stored sampled signal value to a preset value under control of a read signal after read of the stored value, each audio channel unit and said storage buffer are connected to a comparator, said comparator being provided for comparing a sampled signal value supplied by an audio channel with the stored sampled signal value for that audio channel and for generating a writing signal if said supplied sampled signal value has a higher absolute signal value than said stored sampled absolute signal value, said storage buffer being provided for storing said supplied sampled signal value under control of said writing signal.

3. A cochlear implant comprising M (M>1) electrode contacts and a signal processor having a set of N audio channel units and being provided for the conversion, according to a frequency related tonotopic division, of sound signals, each audio channel being provided for applying a frequency related filtering to said sound signal, each audio channel having an output associated with a second sampling unit provided for sampling at a audio channel associated sampling rate the signal output by its associated audio channel unit and writing them into a storage buffer, each second sampling unit being connected with said storage buffer provided for temporarily storing sampled signal values supplied by its associated second sampling unit, characterised in that said storage buffer is connected with a stimulation channel configuration unit provided for defining stimulation channels in order to create electrical fields along auditory neural structures, said stimulation channel configuration unit being further provided to allocate to each stimulation channel at least two of said electrode contacts, to each stimulation channel there being assigned a memory element provided for storing a waveform pattern and a wave duration according to and during which an intensity value determined on the basis of the sampled signal value attributed to the considered stimulation channel is applicable to the electrodes assigned to the considered stimulation channel, said memory element being further provided for storing a maximum value for said intensity value indicating a maximum field strength for the considered stimulation channel and a first and second field identifier identifying a field spread in a basal and apical direction relative to a position of the electrode contacts of the considered stimulation channel.

4. A cochlear implant according to claim 3, characterised in that it comprises a stimulation sequence identifier provided for identifying a set of groups of stimulation channels which are simultaneously stimulatable, the stimulation channels of a same group being selected in order to enable a neural stimulation at neural excitation locations which match with neural excitation locations that would be obtained if the individual stimulation channels of the group would have been stimulated sequentially in time, said stimulation sequence identifier being further provided for cyclically stimulating said groups of stimulating channels.

5. A cochlear implant according to claim 4, characterised in that said set of groups comprises all stimulation channels, each group of to said set comprises all stimulation channels that satisfy said match.

6. A cochlear implant as claimed in claim 4 or 5, characterised in that it comprises an ordering unit provided to order the groups within the set according to sequence defining the order according to which the different groups are sequentially stimulated.

7. A cochlear implant according to claim 6, wherein a time frame is assigned to each group of said set in such a manner that the time frame of the assigned group is at least equal to the waveform duration of the stimulation channel within the considered group having the largest waveform duration.

8. A cochlear implant according to claim 6, wherein said memory element is further provided for storing a neural-repair function H(t), with H(t)=1 for $t<T_{AR}$ where $T_{AR}$ is the total refractery period and $$H(t) = e - \left(\frac{\Delta t - T_{AR}}{\tau}\right)$$

where $\Delta t$ is the stimulus interval and $\tau$ a stimulation channel time constant.

9. A cochlear implant according to claim 5, wherein a time frame is assigned to each group of said set in such a manner that the time frame of the assigned group is at least equal to the waveform duration of the stimulation channel within the considered group having the largest waveform duration.

10. A cochlear implant according to claim 5, wherein said memory element is further provided for storing a neural-repair function H(t), with H(t)=1 for $t<T_{AR}$ where $T_{AR}$ is the total refractery period and $$H(t) = e - \left(\frac{\Delta t - T_{AR}}{\tau}\right)$$

where $\Delta t$ is the stimulus interval and $\tau$ a stimulation channel time constant.

11. A cochlear implant according to claim 4, wherein a time frame is assigned to each group of said set in such a manner that the time frame of the assigned group is at least equal to the waveform duration of the stimulation channel within the considered group having the largest waveform duration.

12. A cochlear implant according to claim 11, wherein said memory element is further provided for storing a neural-repair function H(t), with H(t)=1 for t <$T_{AR}$ where $T_{AR}$ is the total refractery period and $$H(t) = e - \left(\frac{\Delta t - T_{AR}}{\tau}\right)$$

where $\Delta t$ is the stimulus interval and $\tau$ a stimulation channel time constant.

13. A cochlear implant according to claim 4, wherein said memory element is further provided for storing a neural-repair function H(t), with H(t)=1 for t<$T_{AR}$ where $T_{AR}$ is the total refractery period and $$H(t) = e - \left(\frac{\Delta t - T_{AR}}{\tau}\right)$$

where $\Delta t$ is the stimulus interval and $\tau$ a stimulation channel time constant.

14. A cochlear implant comprising M (M>1) electrode contacts and a signal processor having an input for receiving sound signals, said signal processor having a set of N audio channel units which are provided for applying a conversion of said sound signals according to a frequency related tonotopic division and wherein each audio channel unit is further provided for forming audio signal values by applying a frequency related filtering on said converted sound signals, said signal processor further comprising a sampling unit provided for generating for each audio channel unit an audio channel unit dependent sampling frequency (fsi), each audio channel unit having an output connected to a data input of a storage buffer which is provided for receiving said audio signal values sampled at said audio channel unit dependent sampling frequency and for temporarily storing said sampled audio signal values, wherein said signal processor comprises a stimulation channel configuration unit connected with said storage buffer and provided for configurating stimulation channels to create electrical fields along auditory neural structures, said stimulation channel configuration unit being connected to said electrode contacts and further provided to allocate to each stimulation channel at least two of said electrode contacts, to each stimulation channel there being assigned a memory element provided for storing a waveform pattern and a wave duration according to and during which an intensity value determined on the basis of the sampled signal value attributed to the considered stimulation channel is applicable to the electrode contacts allocated to the considered stimulation channel, said memory element being further provided for storing a maximum value for said intensity value indicating a maximum field strength for the considered stimulation channel and a first and second field identifier identifying a field spread in a basal and apical direction relative to a position of the stimulation channel.

15. The cochlear implant according to claim 14, further comprising a stimulation sequence identifier provided for identifying a set of groups of stimulation channels which are simultaneously stimulatable, the stimulation channels of a same group being selected to enable a neural stimulation at neural excitation locations which match with neural excitation locations that would be obtained if the individual stimulation channels of the group would have been stimulated sequentially in time, said stimulation sequence identifier being further provided for cyclically stimulating said groups of stimulating channels.

16. The cochlear implant according to claim 15, wherein said set of groups comprises all stimulation channels, each group of said set comprises all stimulation channels that satisfy said match.

17. The cochlear implant as claimed in claim 15, further comprising an ordering unit provided to order the groups within the set according to sequence defining the order according to which the different groups are sequentially stimulated.

18. The cochlear implant according to claim 15, wherein a time frame is assigned to each group of said set in such a manner that the time frame of the assigned group is at least equal to the waveform duration of the stimulation channel within the considered group having the largest waveform duration.

19. The cochlear implant according to claim 15, wherein said memory element is further provided for storing a neural-repair function H(t), with H(t)=1 for t<$T_{AR}$ where $T_{AR}$ is the total refractery period and $$H(t) = e - \left(\frac{\Delta t - T_{AR}}{\tau}\right)$$

where $\Delta t$ is the stimulus interval and $\tau$ a stimulation channel time constant.

20. The cochlear implant as claimed in claim 14, wherein said storage buffer is connected to a waveform generator which is provided for forming at least one stimulation channel, said waveform generator and said storage buffer being connected to a read signal generator provided for generating read signals enabling to read the stored sampled audio signal values from said storage buffer, said waveform generator being provided for retrieving under control of said read signal said sampled audio signal values of each audio channel unit from said storage buffer and for generating, based on said sampled audio signal values, waveforms having a time period and a wave pattern, said waveform generator being connected to electrode contacts of said cochlear implant and provided for stimulating by means of said waveforms said stimulation channels, wherein said read signal generator is provided for generating read signals asynchronously from said storing into said storage buffer.

21. The cochlear implant as claimed in claim 14, wherein said storage buffer is provided to set a stored sampled signal value to a preset value under control of a read signal after read of the stored audio signal value, each audio channel unit and said storage buffer are connected to a comparator, said comparator being provided for comparing a sampled audio signal value supplied by an audio channel unit with the stored sampled signal value for that audio channel unit and for generating a writing signal if said supplied sampled audio signal value has a higher absolute signal value than said stored sampled absolute audio signal value, said storage buffer being provided for storing said supplied sampled signal value under control of said writing signal.

* * * * *